United States Patent
Sengupta et al.

(10) Patent No.: US 9,134,247 B2
(45) Date of Patent: Sep. 15, 2015

(54) METHOD AND APPARATUS FOR TWO-STEP SURFACE-ENHANCED RAMAN SPECTROSCOPY

(75) Inventors: Atanu Sengupta, New Haven, CT (US); Frank E. Inscore, Bristol, CT (US); Chetan Shende, Ellington, CT (US); Michael J. Donahue, Middletown, CT (US); Stuart Farquharson, Meriden, CT (US)

(73) Assignee: REAL-TIME ANALYZERS, INC., Middletown, CT (US)

( * ) Notice: Subject to any disclaimer, the term of this patent is extended or adjusted under 35 U.S.C. 154(b) by 942 days.

(21) Appl. No.: 13/374,225

(22) Filed: Dec. 16, 2011

(65) Prior Publication Data
US 2013/0157254 A1    Jun. 20, 2013

(51) Int. Cl.
*G01N 21/65* (2006.01)
*G01N 33/58* (2006.01)

(52) U.S. Cl.
CPC .............. *G01N 21/658* (2013.01); *G01N 33/58* (2013.01); *G01N 33/587* (2013.01)

(58) Field of Classification Search
CPC . G01N 21/658; G01N 21/554; G01N 21/648; G01N 21/75; G01N 21/65; G01N 33/587; G01N 33/58; G01N 33/53; G01N 33/543; G01N 33/54393; G01N 33/54346; G01N 33/553; G01N 33/56911; G01N 2035/00158; B82Y 30/00; B82Y 15/00; B82Y 5/00; B82Y 10/00; B82Y 20/00; B82Y 40/00; C12Q 2565/632; C12Q 2537/125; C12Q 1/682; C12Q 2563/155

USPC .......................................... 436/164, 166–172
See application file for complete search history.

(56) References Cited

U.S. PATENT DOCUMENTS

| 5,266,498 | A  | 11/1993 | Tarcha et al. |
|---|---|---|---|
| 6,750,065 | B1 | 6/2004  | White et al. |
| 7,485,471 | B1 | 2/2009  | Sun et al. |
| 7,713,914 | B2 | 5/2010  | Farquharson et al. |

OTHER PUBLICATIONS

Xu et al.,"Surface-enhanced Raman scattering studies on immunoassay", J. Biomed. Optics, 2005, v. 10, No. 3, pp. 031112-1-031112-12.*
Chon et al., "On-Chip Immunoassay Using Surface-Enhanced Raman Scattering of Hollow Gold Nanospheres", Anal. Chem., 2010, v. 82, pp. 5290-5295.*

(Continued)

*Primary Examiner* — Yelena G Gakh
(74) *Attorney, Agent, or Firm* — Ira S. Dorman

(57) ABSTRACT

A SERS method and apparatus employ a sample device having support structure including a first material containing a SER-active metal functionalized with a binding agent having specific capability for binding a designated target analyte. An analyte sample is introduced upon the functionalized SER-active metal; conditions to effect binding of the target analyte to the binding agent are maintained; unbound chemicals, biochemicals, or biologicals are removed; a second SER-active material is introduced to cause it to attach to the bound target analyte; the support structure is irradiated to generate a SER spectrum, with the first and second SER-active materials acting in concert; and the SER spectrum is detected and analyzed to determine the presence and quantity of the target analyte. Alternatively, the second SER-active material may be functionalized with a binding agent, with the procedure being modified accordingly.

29 Claims, 11 Drawing Sheets

(56) References Cited

OTHER PUBLICATIONS

Figure 1:
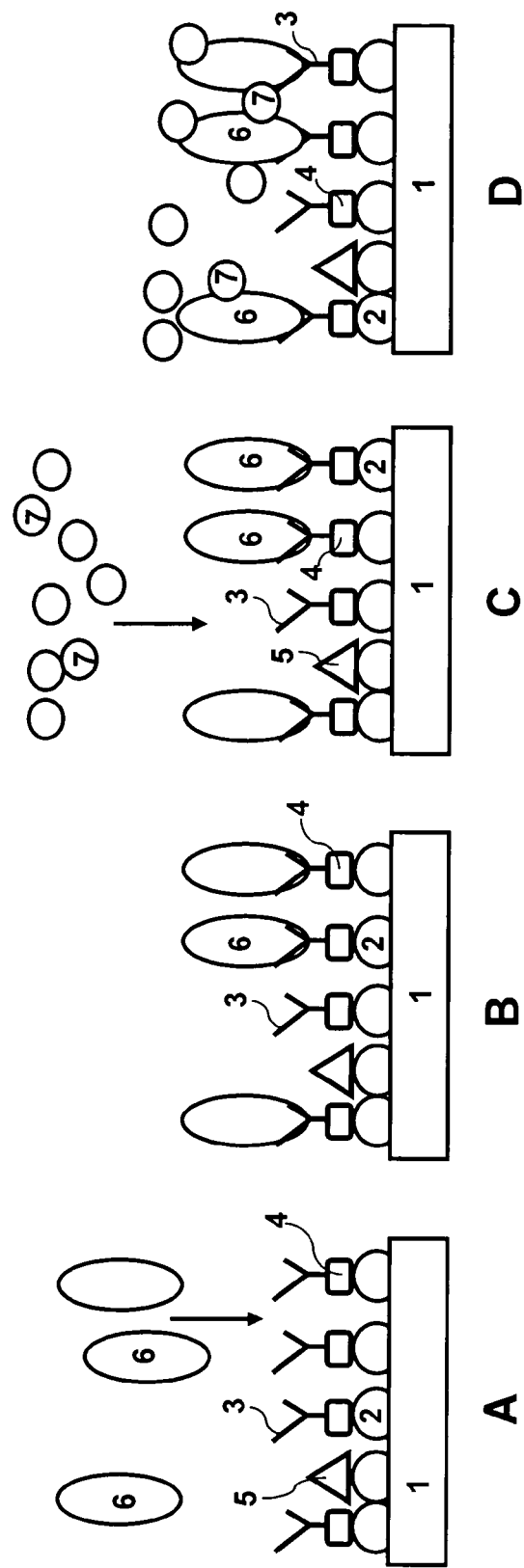
Figure 2A:
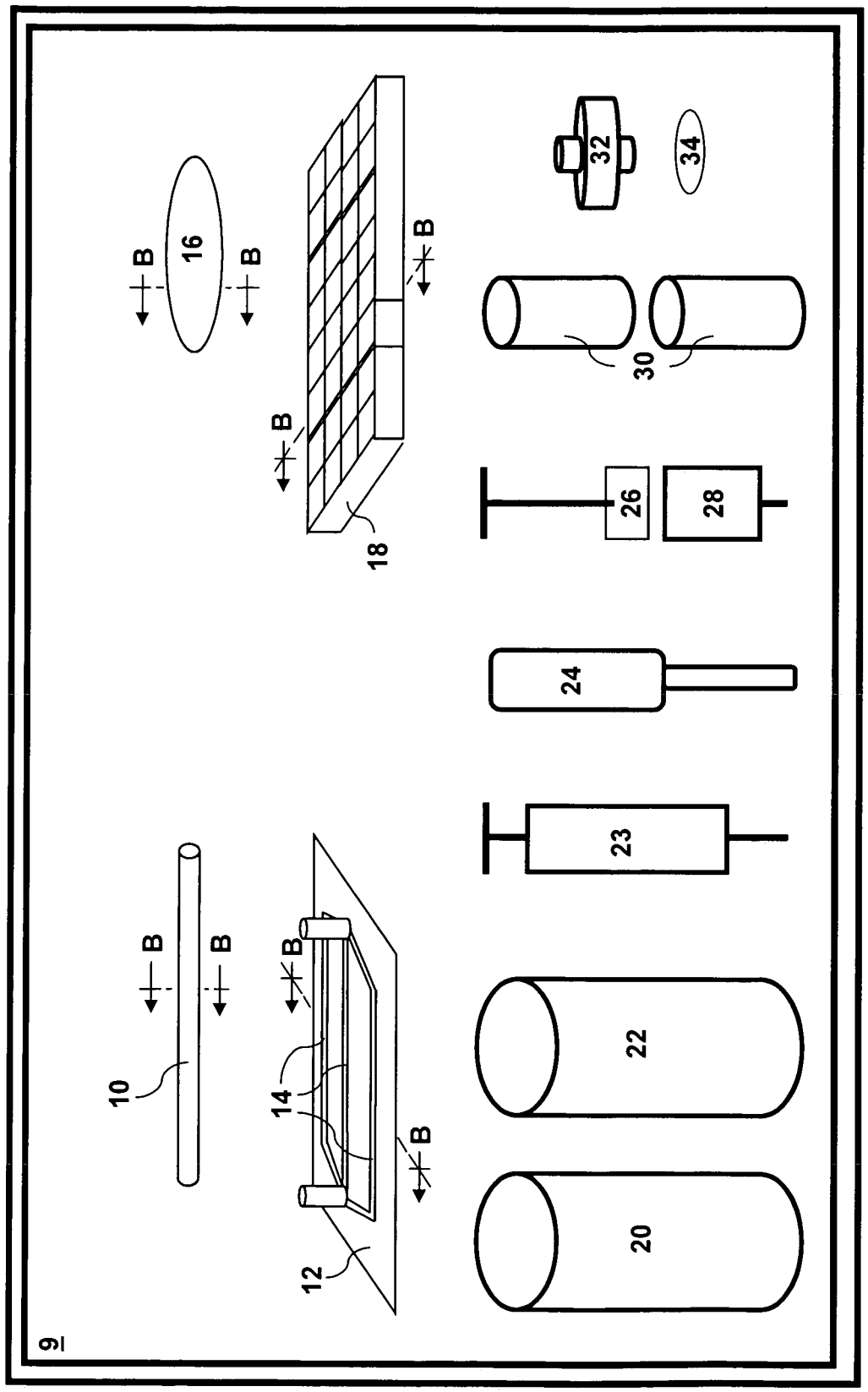
Figure 2B:
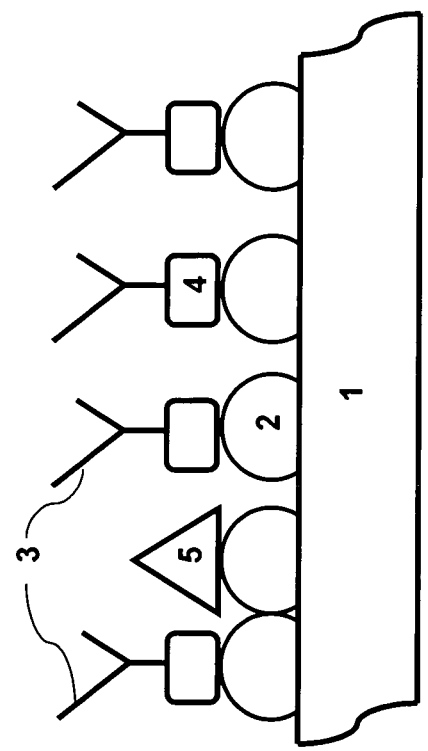

Pekdemir et al.,"Ultrasensitive and selective homogeneous sandwich immunoassay detection by Surface Enhanced Raman Scattering (SERS)† ", Analyst, 2012, v. 137, pp. 4834-4840.*

Chon et al., "SERS-based competitive immunoassay of troponin I and CK-MB markers for early diagnosis of acute myocardial infarction† ", Chem. Comm., 2014, v. 50, pp. 1058-1060.*

"Immunoassay Employing Surface-Enhanced Raman Spectroscopy" Thomas E. Rohr, et al. (Analytical Biochemistry 182, 388-398 (1989)).

"Raman-based detection of bacteria using silver nanoparticles conjugated with antibodies" Ghinwa Naja, et al. (Analyst, 2007, 132, 679-686).

"Protein adsorption drastically reduces surface-enhanced Raman signal of dye molecules" Dongmao Zhang, et al. (J. Raman Spectrosc. 2010, 41, 952-957).

* cited by examiner

METHOD AND APPARATUS FOR TWO-STEP SURFACE-ENHANCED RAMAN SPECTROSCOPY

BACKGROUND OF THE INVENTION

The ability to measure trace quantities of biological materials in a variety of matrices is important to numerous fields. For example, the measurement of a few *Bacillus anthracis* spores in air would be invaluable to homeland security, the measurement *Escherichia coli* in water or *Salmonella enterica* in food would be invaluable to public safety, and the ability to measure disease causing bacteria (e.g. methicillin resistant *Staphylococcus aureus*, MRSA), disease biomarkers or nucleotides in body fluids, such as blood, saliva, or urine, would be invaluable to medical diagnosis. Three methods are widely used to detect such trace quantities of biological material, 1) culture growth of bacteria or viruses that are detected by eye with or without the aid of staining and a microscope, 2) immunoassays in which the binding of an antigen to an antibody is detected or, more recently, 3) polymerase chain reactions in which primers are used to separate target nucleotides, and polymerases are used to generate millions of copies of the nucleotides until they are detectable. The latter two methods often employ fluorescent or radioactive labels for detection.

For most of the applications described above, effective analysis requires speed, sensitivity, selectivity and, ideally, ease-of-use and portability to make at-site measurements. Rapid detection of *B. anthracis* spores in air is required for effective evacuation of potentially exposed personnel; rapid detection of a patient infected with MRSA is required to quarantine the patient and minimize spread of this disease; and rapid detection of *E. coli* in food is required to limit distribution of spoiled food that may cause widespread illness. Extreme sensitivity is also required, as the Department of Defense has estimated that the median lethal dose ($LD_{50}$) for weapons-grade inhalation anthrax is as few as 2,500 *B. anthracis* spores (Defense Intelligence Agency, Soviet biological warfare threat, DST-1610E-057-86, 1986), while $10^6$ colony forming units (CFUs) of MRSA can cause an infection (Freitas, R., "Microbivores: Artificial Mechanical Phagocytes Using Digest and Discharge Protocol", *Journal of Evolution and Technology*, 14, 55-106, 2005), and 100 CFUs of *E. coli* on a food product, considered an infectious dose, can become 1 billion CFUs during a period of just eight hours of transport to market (*E. coli* CFUs double about every 20 minutes, Irwin, P L et al., "Evidence for a bimodal distribution of *Escherichia coli* doubling times below a threshold initial cell concentration", *BMC Microbiology*, 10, 207, 2010). Specificity is also important, in that bacteria within a genus, species, subspecies, strain or serotype, such as *B. cereus* and *S. aureus* (non-methicillin resistant), can give false positive responses for *B. anthracis* and MRSA, members of the same genus and species respectively, using some analytical methods, potentially causing unnecessary anguish or treatment.

Unfortunately, none of the three methods described above can meet the listed requirements: culture growth takes several days, PCR takes several hours, and immunoassays lack sensitivity. In addition, only immunoassays are sufficiently portable for at-site measurements, such as at a military base or a food-processing center.

Recently, several researchers have proposed the use of surface-enhanced Raman spectroscopy (SERS) as the detection method for immunoassays. SERS involves the absorption of incident laser photons within nanoscale metal structures, generating surface plasmons, which couple with nearby molecules (the analyte) and thereby enhance the efficiency of Raman scattering by six orders of magnitude or more (Jeanmaire DL, RP Van Duyne, "Surface Raman Spectroelectrochemistry", *J Electroanal Chem*, 84, 1-20, 1977; or Weaver MJ, S Farquharson, M A Tadayyoni, "Surface-enhancement factors for Raman scattering at silver electrodes: Role of adsorbate-surface interactions and electrode structure", *J Chem Phys*, 82, 4867-4874, 1985).

SERS has been shown to be capable of detecting trace quantities of dipicolinic acid, a chemical prevalent in spores, such as *B. anthracis*, rapidly, and in an easy-to-use format (Farquharson et al., U.S. Pat. No. 7,713,914). However, specificity was limited, and bacilli could not be differentiated from clostridia; and differentiation at the species level (e.g. *B. cereus* versus *B. anthracis*) was not even a consideration. In light of immunoassays, it is reasonable to consider the use of a binding agent, such as an antibody, to selectively bind a target analyte, such as an antigen to achieve species, subspecies, strain or serotype selectivity. The concept was first demonstrated by coating a roughened silver electrode with anti-human thyroid stimulating hormone antibody (anti-TSH) to capture the TSH antigen (Tarcha et al U.S. Pat. No. 5,266,498; 1993). However, "no" SERS of this binding event was shown. Antibody capture was only demonstrated when a second anti-TSH antibody functionalized with a dye (2-[4'-hydroxyphenylazo]-benzoic acid) was added, which itself attached to the bound TSH antibody to produce a spectrum of the dye. Furthermore, the laser wavelength was matched to the absorption of the dye to generate resonance Raman scattering, which, like SERS, is known to enhance Raman scattering by as much as six orders of magnitude. Yet this combined surface-enhanced Raman and resonance Raman spectroscopic (SER(R)S) approach only achieved a modestly low concentration detection of 4 microg/mL ($4\times10^6$ International Units/mL) for the TSH antigen when 40 microg/mL (10 times the concentration) of the dye-anti-TSH complex was added. This result is questionable, since the addition of 40 microg/mL of the dye-anti-TSH complex to a sample containing "no" TSH antigen produced a more intense dye spectrum, suggesting that the spectrum was due more to the dye being in direct contact with the metal surface as opposed through binding to the TSH antigen in forming a dye-(anti-TSH)-TSH-(anti-TSH)-silver complex. In any case, the authors stated that no spectra of antibodies or antigens were obtained, but only spectra of a dye, and antigen-antibody binding typically required an hour or more (two hours for the above example).

In the 19 years since the Tarcha patent there have been only a few publications in which a biochemical of interest, such as those described above, has been successfully bound to an antibody attached to a SERS substrate and detected by SERS. This is due to the fact that the target analyte must be within the plasmon field of the surface-enhanced Raman active (SER-active) metal to achieve a significant enhancement of the Raman signal, since the enhancement decreases with distance to the $12^{th}$ power. This means that the plasmon field extends 10 nm at most. The challenge, and lack of sensitivity, has been elegantly demonstrated for the binding of *E. coli* to an antibody coated on silver nanoparticles (Naja et al., "Raman-based detection of bacteria using silver nanoparticles conjugated with antibodies", *Analyst*, 132, 679 (2007). It was found that the signal was enhanced only by a factor of 20, far less than the expected 1 million or so, even when a very small antibody, Protein A, brought the bacteria to a distance of 8 nm from the metal surface. Furthermore, the *E. coli* sample was allowed to bind (incubate) to the antibody functionalized silver particles "overnight", and dried on a glass slide to concentrate the sample prior to SERS measurements. Clearly, the basic concept of using SERS as the detector for immunoassays does not provide sufficient sensitivity or speed for the applications discussed above.

To overcome the sensitivity limitation, a number of researchers have followed the approach of Tarcha et al, by adding dye molecules to the immunoassay. White et al. (U.S. Pat. No. 6,750,065) describe the use of antibodies that bind drug-dye complexes, such that the introduction of the drug will displace the drug-dye complex, which can be detected "downstream" again using a combined surface-enhanced Raman and resonance Raman spectroscopy approach. The patent details methods to synthesize three drug-dye complexes, but provides no information regarding the antibody nor data showing displacement or the drug-dye complex or the patented principle. Sun et al. (U.S. Pat. No. 7,485,471) describe the use of a dye-labeled antibody that binds a specific antigen, which in turn binds a second antibody that contains a seed particle that, in turn, is used to grow a SER-active particle, which will ideally interact with the dye. No data are supplied, such as the time required to grow the SER-active particle or how the dye will come to interact with it. Consequently, neither of these patents addresses the rapid decrease in signals due to distance from the metal nor the long binding times. In fact the value of using a dye label to increase sensitivity has been questioned by Zhang et al. ("Protein adsorption drastically reduces surface-enhanced Raman signal of dye molecules", *J Raman Spectrosc*, 41, 952, 2010), who have shown that the SER signal intensity of dye-protein complexes added to silver colloids is "reduced" by several orders of magnitude compared to the dye by itself. They showed that a flourescein dye attached to either bovine serum albumin, lysozyme, trypsin, or concanavalin A produced "no" SER signal. Furthermore, they suggest that the signals observed for the other dyes used in their experiments may have resulted from the dyes coming into direct contact with the silver colloids, as the proteins were not bound to the silver colloids before introduction of the dye.

Based on the foregoing, it is believed that one of ordinary skill in the art would not expect a significant SER signal to be generated from an antibody-antigen pair bound to SER-active particles (especially when the antigens are micron-sized bacterial cells), even with the introduction of additional SERS particles after binding has been achieved; nor would the signal strength be expected to be sufficient to detect as few as 10 bacterial spores or CFUs; nor would it be expected that detection could occur in less than 20 minutes, i.e. without a long incubation time.

SUMMARY OF THE INVENTION

It is the broad object of the present invention to provide a novel method and apparatus for detecting, identifying, analyzing, and quantifying target analyte(s), i.e., chemical, biochemical, or biological substances, in test samples.

It is a more specific object of the invention to provide such a method and apparatus wherein detection and analysis are effected by surface-enhanced Raman spectroscopy, with substantial selectivity, sensitivity, and speed, through the use of target analyte-specific binding agents and multiplicative signal enhancement.

It has now been found that the foregoing and related objects of the invention are attained by the provision of a method and apparatus in which an analyte-specific binding agent is attached to at least one of a first SER-active material, of which a support structure is comprised, and a second SER-active material comprising a liquid reagent. An analyte sample is added to one (or both) of the functionalized SER-active materials, and the liquid reagent is added to the support structure such that the SER-active materials are effectively attached to the target analyte so as to act in concert to cooperatively produce greatly enhanced SER signals.

More specifically, certain objects of the invention are attained by the provision of a method for the detection, identification, analysis and quantitation, by surface-enhanced Raman spectroscopy, of at least one designated target analyte, comprising the steps: providing a support structure comprised of a first, SER-active metal-containing SER-active material; providing a liquid reagent comprised of a second, SER-active metal-containing SER-active material; functionalizing the SER-active metal of at least one of the first and second SER-active materials with at least one binding agent that has a specific capability for binding thereto at least one designated target analyte, to provide at least one functionalized SER-active material; obtaining an analyte sample suspected of containing the at least one designated target analyte; adding the analyte sample to one of the at least one functionalized SER-active materials; establishing or maintaining conditions sufficient to effect attachment of the at least one designated target analyte to the at least one binding agent of the one functionalized SER-active material; effecting the removal of any unbound chemicals, biochemicals, or biologicals from the one functionalized SER-active material to which the at least one target analyte is attached; adding the liquid reagent to the support structure; establishing or maintaining conditions effective to cause the other of the first and second SER-active materials to attach to the at least one target analyte already attached to the at least one binding agent of the one functionalized SER-active material; irradiating the first and the second SER-active materials attached to the at least one target analyte so as to cause the SER-active metals of the SER-active materials to cooperatively generate a SER spectrum; detecting the cooperatively generated SER spectrum; and analyzing the detected SER spectrum to determine the presence and quantity of the at least one designated target analyte.

In preferred embodiments the effects of the SER-active metals of the first and second SER-active materials, in cooperatively generating the SER spectrum, are synergistic. That is, multiplicative enhancement, that is quite superior to the sum of the enhancements of the two individual SER-active materials (both of which have been shown to produce insignificant enhancement [vide supra and infra]), are unexpectedly produced.

One or both of the SER-active materials can be used in solution to carry out the method of the invention. However, in most cases one SER-active material will be attached to a support structure to which the other SER-active material is added. Furthermore, in most cases the supported SER-active material will normally be functionalized with the binding agent, but alternatively the added SER-active material could be functionalized and, in some cases, both SER-active materials could be functionalized.

The support structure employed in the method will usually comprise a substrate, supporting the "first" SER-active material, that is functionalized with the "at least one" binding agent.

The substrate may be fabricated from metal, glass, paper, plastic, or any suitable material that may be in the form of a substantially planar sheet or plate, or membrane, or (in the case of glass and plastic) in the form of a wall of a vial, capillary, channel, or the like. A substantially planar sheet or plate may, in some instances, desirably be formed with a multiplicity of wells for receiving the analyte sample or samples. The planar sheet or plate may, in some instances, be porous so as to form a membrane capable of passing the sample through it.

The "first" SER-active material attached to a substrate will generally be of a form selected from: metal colloids as isolated spheres, clusters, aggregates, monolayers, multilayers, ring or tube structures deposited on the substrate; metal-coated particles, monospheres, or lithographically produced structures, such as posts or pyramidal structures on the substrate; metal depositions of islands on the substrate; electrochemically generated metal surfaces; structure defining holes in metal surfaces; metal grown structures on the substrate, including porous metal structures; and metal-doped porous materials. Specific examples include gold and silver colloids, silver coated on a monolayer of polystyrene monospheres, gold-coated lithographically produced silica posts, evaporated silver islands on glass, copper electrodes, silver-doped sol-gels, nickel-coated polystyrene beads on support structures, and gold-doped swellable polymers.

Preferably, the first SER-active material will be composed of at least one SER-active metal and at least one porous material. The latter material will be sufficiently porous to readily pass the "at least one" binding agent, the "second" SER-active material, the "at least one" designated target analyte, and any signature chemical that may be present. In certain instances, the porous structure will advantageously be effective to separate or extract the "at least one" designated target analyte from other components of the analyte sample.

In some preferred cases the binding agent will be attached to the metal of a SER-active material using a linker chemical, chemical functionality, or biochemical; specific examples include cysteine, a thiol group, or N-hydroxy succinimide esters. In other preferred cases the binding agent will be attached to the metal of a SER-active material using a spacer chemical to improve performance of the binding agent by spacing the binding agent a sufficient distance above, or otherwise away from, the SER-active metal surface to bind the target analyte without interference or restriction from the metal surface. For example, it may be beneficial to use a spacer chemical to extend a peptide, as the binding agent, above the surface by several angstroms, such that the binding agent has room to bind the target analyte. Exemplary spacer chemicals are aliphatic thiols, which can self-assemble on the SER-active material to form a monolayer. In those instances the length of the aliphatic chains determines the distance between the SER-active metal surface and the binding agent, which will typically be between 2 and 5 angstroms. Another strategy to increase the distance between the SER-active metal and the binding agent involves adding terminal groups on the binding agent (e.g., amino acid residues for proteins and peptides, and bases for oligonucleotides).

In certain embodiments it may be useful to add a blocking agent to a SER-active surface. Such an agent will serve to block the adsorption of potentially interfering chemicals, biochemicals, or biologicals, preferably without itself producing a SER spectrum. Examples of suitable blocking agents are ethanolamine, polyethylene glycol, polylysine, and bovine serum albumin.

Each of the "first" and "second" SER-active materials employed in the method of the invention will usually comprise a metal selected from the group consisting of copper, gold, silver, nickel, platinum, rhodium, iron, ruthenium, cobalt, nickel, palladium, and alloys and mixtures thereof. The metal of the "first" SER-active material will normally be of particulate form or in the form of a surface having a morphology that is functionally equivalent to metal particles so as to generate a plasmon field when irradiated. The metal of the "second" SER-active material will normally be of particulate form, and will advantageously have an electropotential that is effective to attract it to the bound "at least one" target analyte. It will be appreciated that the "first" and "second" SER-active materials may (or may not) be different from one another, and that the "first" SER-active material may comprise a mixture of at least one SER-active metal and at least one porous material.

The "at least one" designated target analyte and the "at least one" binding agent will normally be a chemical, biochemical or biological substance, and will usually be paired with one another for effective interactions; such pairs may include (a) antibodies and antigens, (b) peptides and biologicals, (c) drug receptors and drugs, (d) enzymes and their specific biochemical substrates (e.g. inhibitors and cofactors), (e) carbohydrates and lectins, and (f) nucleic acid sequences and their complements.

In some embodiments of the present method the "at least one" target analyte will be a bioagent, food or waterborne pathogen, or a disease-causing pathogen. As the term is used herein, "bioagents" include, but are not limited to, *Bacillus anthracis* (including Ames and UT500 strains), *Brucella melitensis* subspecies *and* serotypes (e.g. abortus, suis), *Clostridium botulinum* A, Ebola virus, *Francisella tularensis*, *Leishmania* genus, Marburg virus, *Mycobacterium leprae* (leprosy), Puumala hantavirus, Ricin toxin, Variola virus (small pox), and *Yersinia pestis*.

Food and waterborne pathogens referred to herein, include, but are not limited, to *Aeromonas hydrophilia, Bacillus cereus, Campylobacter jejuni, Clostridium botulinum* B and C, *Clostridium difficile* and *perfringens, Cryptosporidium parvum, Escherichia coli* (O157:H7), *Giardia lamblia*, Hepatitis A, *Listeria monocytogenes* and subspecies and serotypes, *Salmonella enterica* and subspecies and serotypes, including typhimurium, *Shigella dysenteriae* and subspecies and serotypes, *Vibrio cholera*, and *Yersinia enterocolitica*, Disease-causing pathogens referred to herein include, but are not limited to, *Burkholderia mallei* (glanders), coronaviruses (Severe Acute Respiratory Syndrome (SARS)), *Corynebacterium diphtheriae*, Dengue fever, Enteric viruses, *Enterobacter aerogenes, Equine encephalitis*, hemorrhagic fevers, Hepatitis (A-E), herpes simplex viruses 1 and 2, human immunodeficiency virus, Legionella, Lyme *borreliosis* (disease), measles, meningitis, mumps, MRSA, *Mycobacterium tuberculosis, Mycoplasma pneumonia, Neisseria gonorrhoeae*, Norwalk virus, Orthomyxoviridae family (influenza), *Plasmodium* genus (Malaria), rabies virus, rhinoviruses, *Rickettsia* species (e.g. rickettsii, prowazekii, typhi), Rotovirus, Rubella virus, saxitoxin, sepsis, *Shigella*, and subspecies and serotypes, *dysenterial, Staphylococcal* (*enterotoxin B, agalactiae*, and *pyogenes*), *Streptococcus pneumonia*, Swine disease, *Treponema pallidum* (syphilis), *Varicella zoster* virus (chicken pox, shingles), West Nile virus, and Yellow fever.

In certain embodiments the method will include a further step of adding to the analyte sample at least one reagent that is effective, under the conditions existing or established, for releasing a signature chemical, a signature biochemical, or a signature biological, with the signature chemical, biochemical or biological thus constituting the "at least one" designated target analyte. More specifically, the "at least one" target analyte may be a released signature chemical selected from the group consisting of calcium dipicolinate, dipicolinic acid, mono-protonated dipicolinic acid, deprotonated dipicolinic acid, diaminopimelic acid, n-acetyl-muramic acid, ribonucleic acid, phosphoglyceric acid, and sulfoacetic acid. Examples of released signature biochemicals include amino and nucleic acids, nucleotides, nucleosides, deoxyribonucleic acid, ribonucleic acid, gene sequences, plasmids, phages, peptides, proteins, lipids, polysaccharides, haptans, antibodies, antigens, biomarkers, enzymes, steroids, hormones, lectins, aptamers, including fragments or polymers thereof (e.g. antibody-fragment, polypeptides).

The reagent for effecting release of a signature chemical, biochemical, or biological, will normally be an acid, base, or solvent, or mixture thereof. Example acids include acetic, adipic, ascorbic, citric, formic, fumaric, lactic, malic, palmitic, peracetic, propionic, salicylic, sorbic, succinic, and trihaloacetic acids, while example solvents include acetone, acetonitrile, benzene, chloroform, carbon tetrachloride, cyclohexane, dichloromethane, diethyl ether, dimethylsulfoxide, ethyl acetate, ethylene glycol, isopropyl ether, methyl ethyl ketone, n-hexane, phenol and its derivatives, tetrahydrofuran, toluene, and mixtures thereof.

Additional objects of the invention are attained by the provision of apparatus, in the form of a kit of components, for use in the detection, identification, analysis, and quantitation of at least one designated target analyte in an analyte sample, by surface-enhanced Raman spectroscopy. The apparatus comprises: packaging means for the containment of a multiplicity of components (i.e., normally containing all components of the kit); at least one SER-active sample device component constructed for receiving the at least one designated target analyte, and for operative assembly with a Raman spectrometer to enable detection, identification, analysis, and quantitation, by surface-enhanced Raman spectroscopy, of at least one designated target analyte; at least one collection component that is constructed for analyte sample collection and discharge; at least one container containing a liquid reagent comprised of the second SER-active material; additional containers containing reagents; a component for introducing the liquid reagent into the SER-active device component; and optionally additional components, such as sample transfer components, mixing containers and filtering apparatus, as needed. The apparatus will usually comprise a plurality of collection components contained by the packaging means, such as eyedroppers, syringes, pipettes and micropipetters, and swabs, or a multiplicity of such components assembled in various combinations. Preferably, the kit will additionally include a water-supply component comprised of a container containing distilled, deionized water, at least one mixing container, and a filtering component for filtering an analyte sample. In most instances the apparatus will additionally include at least one second reagent supply component, comprised of a container containing, for example, a buffered solution to maintain a pH, or an agent to degrade a biological material to effect release of a signature species, such as a signature chemical, a signature biochemical, or a signature biological; in the latter case, the signature species will normally constitute the "at least one designated target analyte," as more specifically identified herein.

The SER-active device component of the instant apparatus is constructed to enable irradiation and collection of Raman scattered radiation by and from a Raman spectrometer. It provides a support structure comprised of the first SER-active material, the SER-active metal of which may be functionalized with at least one binding agent which has the specific capability of binding thereto the at least one designated target analyte, and that is accessible for the deposit thereupon of analyte samples, the second SER-active material, and any additional reagents employed; it may advantageously comprise a vial, capillary, disc, multi-well plate or lab-on-a-chip (LOC) device. The disc or multi-well plate may be made of a porous membrane, so as to pass the sample through it. As previously noted, rather than functionalizing the metal on a support structure, or in addition thereto, the metal of the SER-active material comprising the liquid reagent may be functionalized with at least one binding agent.

As also indicated above, a linker or a spacer chemical or biochemical will, in some instances, preferably be interposed between the binding agent and the associated metal of a SER-active material for attaching the at least one binding agent thereto, and thus may be a feature of the apparatus of the invention; the first and second surface-enhanced Raman active materials employed therein will comprise the metals hereinabove and hereinafter specified. The surface-enhanced Raman active material comprising the support structure may be of particulate form, or in the form of a surface having a morphology functionally equivalent to metal particles, so as to generate a plasmon field when irradiated; the metal of the second surface-enhanced Raman active material will preferably be provided as a colloidal suspension of metal particles in the form of isolated spheres, clusters, aggregates, ring or tube structures. In addition to providing SER activity, the metal particles (or equivalent structure) will desirably also function by reason of having an electropotential that is effective to attract it to the bound designated target analyte. As indicated above, the metals of the first and second surface-enhanced Raman active materials may be different from one another.

As used in the present application, the following terms and references are to be understood to have the meanings hereinafter set forth, unless a different or further definition is provided, or the context makes it clear that another meaning is intended:

"Chemical substance" means any general chemical, including drugs, explosives, radionuclides, pesticides, inorganic or organic pollutants, and their associated precursors or break-down products (e.g. hydrolysis products, metabolites, etc.).

"Biochemical substance" means any biochemical involved in chemical processes of living organisms, including amino and nucleic acids, nucleotides, nucleosides, peptides, proteins, lipids, polysaccharides, haptans, antibodies, antigens, biomarkers, enzymes, steroids, hormones, lectins, aptamers, phages, prions, immunoglobulins, toxins, including fragments or polymers thereof (e.g. antibody-fragment, polypeptides). Specific examples include serum albumin, immunoglobulin G, human thyroid stimulating hormone, and prostate specific antigen.

"Biological substance" means a microbial life form, such as any algae, bacteria, fungi, protozoa, or virus.

As used in respect of a target analyte, "identify" means to determine the chemical, biochemical, or biological identity of the target analyte from cooperatively generated spectra.

"Specificity," as used in respect of a target analyte, refers to the selective binding of a particular target analyte, as opposed to analytes with similar structure that would produce a false positive response. Examples include: (1) selective binding of $B.\ anthracis$, but not other bacteria, especially not clostridia and most especially not other bacilli; (2) $E.\ coli$ O157:H7, but not other bacteria, and most especially not other $E.\ coli$; and (3) or selective binding of cocaine, but not other drugs, and especially not cocaine metabolites, such as benzoecognine.

Exemplary of the sensitivity that is achieved using the method and apparatus of the invention is the ability to detect (i.e., to obtain SER scattering data) and measure $2500/m^3$ $B.\ anthracis$ spores in air, 100 CFUs/mL $E.\ coli$ in lettuce, $10^6$ CFUs MRSA/mL sputum, and 10 ng/mL of a drug in saliva.

The test sample (i.e., a sample containing a target analyte) utilized in carrying out the method of the invention may be obtained from a broad variety of gaseous, liquid, and solid sources. Gas sample sources include, but are not limited to, air, a gaseous chemical, a chemical or biological aerosol, exhaust fumes, ventilation system or room air, exhaled or ventilated breath, extracted lung air, and mixtures thereof; examples of target analytes in specific gas test samples include biological spores or toxic industrial chemicals in air, and bacteria or disease biomarkers in exhaled breath.

Liquid sample sources include, but are not limited to, chemicals, water, and biological fluids such as blood plasma, blood serum, whole blood, exhaled breath condensate, nasal mucus, saliva, semen, spinal fluid, sweat, throat sputum, and urine. Examples of target analytes in liquid test samples include a drug in a chemical solvent; bacteria or pesticides in a drink, such as juice or milk; bacteria in a lake, sewer, or water-treatment sample; a pollutant in a lake, river, ocean, ground water, or rain sample; a drug in blood plasma, saliva, or sweat; a bacterium in nasal mucus, saliva, or throat sputum; and a disease biomarker in semen or urine.

Examples of solid sample sources include, but are not limited to, food, soil, an animal part, feces, a frozen material, and a substance on a surface. Examples of target analytes in solid test samples include bacteria and pesticides in or on fruits, meats, and vegetables; pesticides in soil; poisons in animal kidneys and livers; bacteria in feces; bacterial spores on a mail-sorting machine; explosive materials on or in an improvised explosive device; and drugs and explosives on clothing, luggage, hair, fingertips or fingernails.

The volume of the test sample employed will be defined by the required analysis, and can be quite large or very small. For example, cubic meters of air would normally be collected for the purpose of detecting aerosolized bacterial spores, whereas a drop of saliva would normally suffice for the detection of a drug. The volume of the analyte sample employed will generally be quite small, such as 10 mL; often, however, the volume will not exceed 1 mL, and in many instances it will be much less.

For many test samples the method will desirably include the further step of treating a collected or sampled material or substance (e.g., a test sample) so as to separate the "at least one" target analyte from other components, and to thereby produce an "analyte sample." The residual "other" components will normally constitute all chemicals, biochemicals, and biologicals present in the collected or sampled material that may interfere significantly with analysis. Such interferences include hindering flow of the target analyte(s) to the binding agents, deactivating the SER-active materials, and/or producing spectra that would substantially prevent the spectrum of the at least one target analyte from being observed. Such a further treating step may include the use of an extracting or degrading chemical effective to make the "at least one" target analyte available, and means for separating the at least one target analyte from the chemical used for extracting or degrading.

In the case of solid test samples, the extracting or degrading chemical may be selected from the group consisting of acids, bases, solvents, and combinations thereof. Examples include acetic acid to release dipicolinic acid (DPA), a signature for endospores, and a chloroform and phenol mixture to release DNA from bacteria, DPA and DNA being a signature chemical and a signature biochemical for these pathogens, respectively.

In the case of body fluids, the extracting or degrading chemical may be selected from the group consisting of solvents, acids, bases, mucolytic agents, surfactants, and mixtures thereof. Suitable mucolytic agents include N-acetyl-L-cysteine (NALC), Amboxol, Bromhexine, and combinations thereof a solution of NALC and NaOH is presently preferred for separating drugs from saliva.

In some cases a combination of reagents may be used. For example, mucolytic agents used to separate $B.$ $anthracis$ spores from sputum followed by the use of acetic acid to release dipicolinic acid.

In the case of many gaseous, chemical, and water test samples, the target analyte will inherently be available for separation, and an extracting chemical need not be used. Specific examples include bacterial spores in air, drugs in a solvent, and pesticides in water.

Target analytes, and other components, may be mutually separated from the produced degrading chemical solution using a chemical, physical, or chromatographic method.

Chemical treatment of a sample may employ a solvent for the at least one target analyte, which solvent will desirably be of such polarity as to render it capable of extracting the target analyte. Suitable solvents include water containing appropriate acids and bases for pH adjustment; organic liquids such as acetone, acetonitrile, benzene, chloroform, carbon tetrachloride, cyclohexane, dichloromethane, diethyl ether, dimethylsulfoxide, ethyl acetate, ethylene glycol, isopropyl ether, methyl ethyl ketone, n-hexane, phenol and its derivatives, tetrahydrofuran, and toluene; and mixtures of such solvents.

Physical treatment for effecting mutual separation may involve passage of the sample through a filter. Suitable filters comprise porous substrates such as paper, coated paper, paper fibers, polymer, polymer fibers, mixed paper and polymer fibers, cellulose acetate, glass wool, cotton, diatomite, porous glass, sintered glass, zirconia-stabilized silica, derivatized silica-based matrices, sol-gels, and derivatized sol-gels. They may also comprise a supported membrane covered with separation materials, such as the silica gels, zirconia-stabilized silica, derivatized silica-based matrices, sol-gels, derivatized sol-gels, glass beads, long-chain alkane particles, derivatized long-chain alkane particles, polymers, derivatized polymers, functionalized membranes, alumina, polystyrene, dendrimers, immobilized crown ethers, and ion-exchange resins.

Chromatographic methods may employ the same separation materials, and will desirably utilize a liquid carrier solvent for at least one of the target analytes.

The "first" SER-active material referred to herein will desirably be attached to a support structure that provides a solid surface, as described. It will, in general, consist of a SER-active metal in the form of particulates or coatings on surface or in matrices or solutions, or other appropriately sized structures that can generate a surface plasmon field when irradiated. Effective forms of SER-active metals can be produced by chemical or electrochemical etching, by photolithographic process, by vapor or chemical deposition, by reduction of metal salts, or by other means known to those skilled in the SERS arts.

The added "second" SER-active materials will generally be of a form selected from metal colloids or monospheres, or metal coated spheres in solution as isolated spheres, clusters, aggregates, or ring or tube structures. Specific examples include silver colloids, aggregates of colloids, gold-coated polystyrene spheres, and gold-coated magnetic iron beads.

The SER-active metal of at least one of the "first" and "second" SER-active material should, in any event, be readily functionalized with a suitable binding agent; i.e., a chemical, biochemical, or biological substance that binds, or attaches, to a specific target analyte. Such functionalization generally includes the formation of a chemical bond or physical interaction, including covalent, ionic, hydrogen bonds, or van der Waals or electrostatic forces, between the metal and the binding agent.

Porous materials that contain SER-active metals and that comprise the "first" SER-active material can be produced by chemical synthesis, using methods that include sol-gel chemical syntheses employing silica-based alkoxides and SER-active metals, and polymer syntheses employing hydrophilic monomers that allow the inclusion of SER-active metals. Such a SER-active material may also be a porous volume produced by mixing a porous medium and a SER-active metal; such media include sol-gels, silica gels, silica stabilized by zirconia, derivatized silica-based matrices (e.g., trifunctional quanternary amine, aromatic sulfonic acid), long-chain alkane particles (e.g., C8 to C18), derivatized long-chain alkane particles (e.g., phenyl, cyano, etc.), and other porous media commonly known to one skilled in the art of porous media. Preferably, such a metal-doped porous material will be sufficiently porous to permit liquids (e.g., the target analyte, and liquid reagents comprising the "second" SER-active material) to be transported therethrough to the first SER-active metal sites. Such a porous material may advantageously be of a chemical composition that is effective to extract a target analyte from a test sample (treated as necessary), to thereby improve sensitivity (i.e., the effective detection of a targent analyte by SER scattering, in the concentration present).

Desirably, an alkoxide is used to produce a polar-positive, polar-negative, or non-polar sol-gel that is effective in extracting the appropriately charged or neutral target analyte. Suitable alkoxides include but are not limited to tetramethyl orthosilicate, tetraethyl orthosilicate, methyltrimethoxysilane, methyltriethoxysilane, aminopropyltriethoxysilane, aminopropyltrimethoxysilane, octadecylsilane, etc. Additional selectivity for extraction can be imparted using polymers (e.g. polydimethylsiloxane for extractions using hydrophobic interactions, and polyethylene glycol (PEG) for extractions using hydrophilic interactions).

A non-functionalized SER-active material, used in the practice of the present invention, will desirably have an electropotential that is effective to attract it to the target analyte that is attached to the functionalized SER-active metal. Examples of materials having such an electropotential include electropositive silver colloids, effective to be attracted to negatively charged target analytes, target analyte functional groups, or target analyte surface sites; and electronegative gold coated polystyrene spheres, effective to be attracted to positively charged target analytes, target analyte functional groups, or target analyte surface sites.

Binding attachment may occur through chemical bonds or physical interactions, such as covalent, ionic, or hydrogen bonds, or by van der Waals or electrostatic forces between charged, polar, hydrophobic, or hydrophilic chemical groups on the surface of the at least one analyte and binding agent. Binding usually occurs within a period of 60 minutes after introduction of an analyte sample to a functionalized SER-active material, under conditions sufficient to effect the necessary interaction; preferably, however, attachment will occur within a period of 10 minutes, and most preferably within a 5-minute period. These binding times are indicative of the speed with which the steps of the present method can be effected.

As previously indicated, the method of the invention will usually include a wash step, using a suitable solvent, for effecting removal of any unbound or unwanted chemicals, biochemicals, or biologicals that may interfere significantly with the measurement that is to be made. Such suitable solvents include water having a selected pH value (e.g. using a buffer), acetone, acetonitrile, benzene, chloroform, carbon tetrachloride, cyclohexane, dichloromethane, diethyl ether, dimethylsulfoxide, ethyl acetate, ethylene glycol, isopropyl ether, methyl ethyl ketone, n-hexane, tetrahydrofuran, toluene, and mixtures thereof. The wash step will usually require a period of no more than 30 minutes, preferably no more than 5 minutes, and most preferably no more than 1 minute.

The second SER-active material is added to the first promptly after the designated target analyte has been allowed to attach to the functionalized SER-active material (whether it is on a support structure or in a liquid reagent). When a wash step is employed, addition of the second SER-active material will most desirably be performed as soon as it is feasible to do so; usually within 10 minutes, and preferably within 1 minute, and most preferably as soon as the wash step is complete. These time periods are also indicative of the speed with which the instant method can be carried out.

The support structure will desirably be so constructed as to effectively enable irradiation of the target analyte, combined with the first and second SER-active materials, and the collection of the cooperatively generated spectrum. Irradiation is preferably effected using a laser, and the generated SER signal is detected by a Raman spectrometer. The Raman spectrometer may be scanning or optical filter, preferably interferometric or dispersive in design, and capable of producing spectra using a strip chart recorder, a plotter, or preferably a computer with appropriate software.

The objective of analyzing the detected spectra, to determine at least the presence of the target analyte in the sample, will normally be achieved based on the spectral peak positions of the target analyte, when a SER spectrum matches, automatically or manually, a previously measured spectrum of the target analyte, which most often will be stored in a spectral library. In some instances, the spectral differences within a genus between two species, subspecies, strains or serotypes, will be subtle and chemometrics will be used to identify the particular species, subspecies, strains or serotypes; augmentation of the method by the application of chemometric techniques can also assist in determining pathogenicity, potency, and toxicity and viability. Chemometrics, suitable for the present method, will typically involve measuring numerous spectra of the species, subspecies, strains or serotypes to be differentiated and applying statistical analysis to the spectra so that differences can be modeled, then using the model to categorize an unknown measured target analyte as a particular species, subspecies, strain or serotype.

Quantitation of the target analyte (i.e., determining the amount present) is achieved by measuring the SER spectral intensity. Spectral intensity can be a peak height or area, or a combination of peak heights or areas, in some cases compared by ratio to a spectral intensity of an internal or external reference material. Such an internal reference will preferably be a solvent in which a target analyte is contained, or the signal produced by the binding agent. An external reference may be a chemical added specifically for the purpose of providing a reference, or software that compares the spectral intensity to a previously measured concentration sample set.

Needless to say, sample collection and treatment, addition of the sample to the SER-active sample device, effecting a wash step, addition of the second SER-active material, addition of any release reagent, irradiating the structure, detecting the SER scattering, and analyzing the acquired spectrum to detect, identify, analyze, and quantify the target analyte, will all desirably be performed with substantial selectivity, sensitivity, and speed. Those desiderata are enabled by the present invention, as described herein.

With further regard to the kit of components embodying the apparatus of the invention, such components will usually include, in general terms, means for obtaining a test sample;

means for treating the sample to effect mutual separation of at least one target analyte and interfering chemicals, biochemicals, or biologicals, to produce an analyte sample; means for introducing the analyte sample to a support structure that contains a first SER-active material; means for introducing a wash solution to remove any unbound chemicals, biochemicals or biologicals; means for adding a second SER-active material; and, optionally, means for adding an additional reagent to make available signature chemicals, biochemicals or biologicals. Apparatus embodying the invention may also include means for irradiating the support structure and target analyte to generate a spectrum; a spectrometer for collecting and detecting the generated spectrum; and means for analyzing the spectrum to detect, identify, analyze, and quantify the target analyte, if present.

The support structure comprising the apparatus may advantageously include at least one section for combining the analyte sample with a binding agent, the wash solution, the second SER-active material and, if appropriate, a signature chemical releasing agent. In certain embodiments, such a section for combining will be in direct liquid flow communication with the means for sample treating; it may either be physically separated from the section by which radiation is enabled, or the two functions may be performed by a single component. In some embodiments it may be desirable to detect and quantify more than one target analyte. In such cases the support structure employed may contain multiple sections, each having a first SER-active material, which may be functionalized with analyte-specific binding agents; multiple sections may take the form of wells in a multi-well plate; multiple channels in a lab-on-a-chip (LOC), either in sequence or in parallel; or multiple segments, in sequence, within a capillary.

The optical interface between the SER-active sample device and the Raman spectrometer will of course be designed to enable irradiation of the SER-active metals and target analyte, and collection of the generated Raman scattering in a manner appropriate to the device. Examples include a simple lens, a cylindrical lens, a microscope objective, a fiber optic probe, etc. A single lens can be used to focus the laser to a point in the device and to collect the Raman radiation. This would be appropriate for a SER-active sample device having a single measurement point, such as a SER-active disc, capillary, vial, or lab-on-a-chip. A single lens system could also be used to measure multiple points on a SER-active sample device, such as a capillary, lab-on-a-chip or multi-well plate, by either moving the lens or the SER-active device, manually or automatically, to align the lens with each measurement point. In some instances a cylindrical lens may be appropriate to allow measurement of multiple points, and hence multiple target analytes, simultaneously on a SER-active sample device. For example, the cylindrical lens could be used to focus the excitation laser in the shape of a line across several parallel channels of a LOC, or wells of a multi-well plate, each channel or well being designed to detect a unique target analyte, and to collect the SER scattered radiation, such that each measurement point is spacially separated along one axis of a two dimensional array detector, the other axis being used to obtain the Raman spectrum as a function of wavenumbers (i.e. wavelength).

Ideally, the support structure and analyzer afford ease of use and portability, for at-site measurements, such as at the site of a bioagent attack or at the bedside of a hospitalized patient.

Exemplary of the utility of the present invention are the following, generalized examples:

General Example A

A surface, representative of surfaces associated with mail facilities (bins used to hold letters, sorting equipment, etc.), hospitals, and the like, is examined to detect potential contamination by bioagents or pathogens. A drop of solvent (i.e., about 50 microliters), such as water, is applied to the surface so that the bioagents or pathogens can be collected in solution and delivered, after being passed through a filter, if appropriate, to a first SER-active material, functionalized with a binding agent, attached to a SER-active sample device. After allowing time for the bioagents or pathogens, if present, to bind to the binding agent (typically, a period of five minutes), a wash solution is drawn through or across the SER-active sample device to remove any unbound chemicals, biochemicals, or biologicals that may be present. Then a second SER-active material, in solution, is drawn into or onto the SER-active sample device. In the case of Bacilli or Clostridia spores, the addition of the second SER-active material may include, or be followed by, a weak acid solution, such as acetic acid, to cause the release of calcium dipicolinate into the solution, and thereby to form dipicolinic acid. The SER-active sample device is then placed within, or attached to, the sample compartment of any suitable Raman spectrometer (as described herein), and the required measurement is performed.

Since the amount of solvent used in the present procedures would generally be known, that information can be used, in conjunction with knowledge of the measured surface area covered, to quantify, in terms of surface area (e.g. 10 spores per $cm^2$), the bioagents or pathogens detected. As an alternative, a swab could be used to wipe a predefined area, the swab then being introduced into a predefined volume of solvent so as to again to enable quantification of the measurement.

A variety of devices can be employed to dispense the solvent, to collect the resultant sample solution, and to deliver the solution to the SER-active sample device. For example, a simple eyedropper, a disposable pipette, a calibrated micropipetter, or a calibrated syringe could be used both to dispense the solvent and also to collect the sample solution; alternatively, a different device, such as a syringe fitted with a particle and/or chemical filter, could be used for collection.

General Example B

In a second manner of use of the present method, air samples are semi-continuously or periodically collected and examined for bioagents or pathogens, and any apparatus that is commonly used to collect and concentrate particles from the air can serve as a sample-acquisition device. In many instances, however, cyclone or impactor devices will be preferred, which may be designed to handle large volumes of air, at high flow rates, and to collect particles within certain size ranges, such as biological particles of 1-20 microns. In any event, such an airborne sample acquisition device would advantageously deposit the collected particles into a vessel containing a solvent, to allow treatment and introduction to a SER-active sample device, as previously described. It will also be appreciated by those skilled in the art that wet-walled cyclones, designed to efficiently capture particles and transfer them to an underlying container, could be employed to particularly good advantage; the solvent used for sample collection could then serve as the wall-washing solution.

To enable continuous monitoring, collected bioagents or pathogens could be deposited upon a rotating carousel holding numerous containers of solvent, into a solvent stream, or upon a moving tape to which the solvent is added. In the first case, the content of each container could be analyzed as described above, manually or automatically. In the case of a solvent stream, the sample could be passed through a filter to remove interfering or extraneous collected particles, and then passed into a series of capillaries or channels within a LOC in a series of steps; e.g., stopping the flow to allow binding; washing the surface; introducing the second SER-active material; making SERS measurements, and then resuming the flow, generally to an unused LOC. In the case of a moving tape, an appropriately placed source of solvent could be added to remove the bioagents or pathogens from the tape, and deliver the resultant sample to the support structures described above, with the appropriate steps, such a, a wash step, a step of introduction of a second SER-active material, a release agent, etc. In any event, the SER-active sample device, such as capillaries, LOCs, or multi-well plates, would be aligned, or otherwise associated, with the irradiating source of any suitable Raman spectrometer, to enable the required measurement to be performed.

General Example C

In another mode of use of the instant method, the target analyte-containing sample is obtained from blood, blood plasma, feces, nasal mucus, saliva, semen, sweat, throat sputum, urine, or other biological matter; examples of typical target analytes are hospital pathogens, disease biomarkers, drugs, and drug metabolites. Samples are acquired using appropriate means, e.g., a swab for collecting sweat, and additional means may be desirably employed to separate the pathogens from the body fluid prior to introduction of the sample to the support structure. When, for example, a swab is used to collect a sample, a non-cotton swab (e.g., having a polyester absorbent element) will generally be preferred because cotton fibers tend to plug pores of separation media. The swab, or other implement used for collection, is weighed before and after collection to determine the sample mass, and thereby allow results to be quantified.

Nasal mucus, saliva, and throat sputum are composed largely of water (about 95%) and mucins, otherwise known as glycoproteins (about 0.5-2%) (Kaliner, M, Z Marom, C Patow, "Human respiratory mucus", *J Allergy Clin Immunol,* 73, 318-323, 1984). The mucins consist of a protein core (about 20%) with oligosaccharide side chains (about 80%), crosslinked by disulfide and hydrogen bonds, which give mucus, saliva, and sputum their high viscosity.

To best enable analysis of nasal mucus, saliva, and throat sputum, mucins should be broken down, or "liquefied," to separate the target analyte, such as spores or drugs, that may be present (see for example; Kubica, G, A Kaufmann, W Dye, "Comments on the use of the new mucolytic agent, N-acetyl-L-cysteine, as a sputum digestant for the isolation of mycobacteria", *Am Rev Respir Dis,* 87, 775-779, 1964; or Murray, P, E Baron, J Jorgensen, M Pfaller, R Yolken, Manual of Clinical Microbiology, $5^{th}$ ed, ASM Press, Washington D.C., 1995). Nasal mucus, saliva, and throat sputum may be chemically degraded, to allow mutual separation of the target analyte(s) and mucin degradants, using mucolytic agents, surfactants, acids and/or bases. Suitable mucolytic agents include N-acetyl-L-cysteine (NALC), Amboxol, Bromhexine, or any combination thereof; in many instances, a solution of NALC and NaOH will preferably be employed. The surfactant utilized may advantageously be lithium dodecyl sulfate, sodium dodecyl sulfate, or a combination thereof, and an acid or base employed may be HCl, $H_2SO_4$, $HNO_3$, NaOH, or KOH, or any combination consisting of such acids or bases.

Nasal mucus, saliva, and throat sputum degradants and the target analyte may be separated by chemical, physical, or chromatographic methods, or any combination thereof. Chemical methods will typically employ a solvent to extract the target analyte from the degradants, such as water having a selected pH value, acetone, acetonitrile, benzene, chloroform, carbon tetrachloride, cyclohexane, dichloromethane, diethyl ether, dimethylsulfoxide, ethanol, ethyl acetate, ethylene glycol, isopropyl ether, methanol, methyl ethyl ketone, n-hexane, tetrahydrofuran, toluene, and mixtures thereof; mixtures that aid in selectively extracting the target analyte into a desired solvent are especially desirable.

Physical separation methods will typically employ a filter that captures the degradants while allowing the passage of the target analyte. Suitable filters comprise a porous substrate or other element, such as paper, coated paper, paper fibers, polymer, polymer fibers, mixed paper and polymer fibers, cellulose acetate, glass wool, cotton, diatomite, porous glass, sintered glass, zirconia-stabilized silica, derivatized silica-based matrices, sol-gels, and derivatized sol-gels.

Chromatographic techniques suitable for use will typically employ a separation material, contained in a column, through which the degradants and target analyte pass at different flow rates. Such chromatographic separation materials include silica gels, zirconia-stabilized silica, derivatized silica-based matrices, sol-gels, derivatized sol-gels, glass beads, long-chain alkane particles, derivatized long-chain alkane particles, polymers, functionalized membranes, alumina, polystyrene, dendrimers, immobilized crown ethers, and ion-exchange resins.

BRIEF DESCRIPTION OF THE DRAWINGS

FIG. 1 is a diagrammatic illustration showing apparatus embodying the present invention, depicted in a series of stages comprising a method embodying the invention.

FIG. 2A is a diagrammatic illustration of an analytical kit embodying the present invention;

FIG. 2B is a diagrammatic, very much simplified illustration, taken generally along lines B-B of FIG. 2A and drawn to a greatly enlarged scale, of a substrate carrying a SER-active material deposit functionalized with a binding agent having a specific capability for binding a target analyte.

FIG. 3 is a diagrammatic illustration showing components of apparatus embodying the invention, depicted in a series of steps comprising a method embodying the invention, for measuring a pathogen sample on a surface by SERS.

FIG. 4 is a diagrammatic illustration showing components of apparatus embodying the invention, depicted in a series of steps comprising a method embodying the invention, for measuring a food sample containing foodborne pathogens by SERS.

FIG. 5 is a diagrammatic illustration showing components of apparatus embodying the invention, depicted in a series of steps comprising a method embodying the invention, for measuring infectious disease pathogens by SERS.

FIG. 6 is a series of four SER spectra obtained for 1000 *B. cereus* spores in a 10 μL sample introduced into four different 1 mm glass capillaries prepared as follows: A) containing *B. cereus* specific peptides functionalized on silver in a sol-gel matrix with silver colloids added after the sample and a wash step; B) identical to A), but no colloids were added; C) identical to A), but no silver particles functionalized with peptide were incorporated in the sol-gel; and D) identical to C), but acetic acid was included in the silver colloid solution. The intensities of the B) and C) spectra have been multiplied by 10, while the intensity of the D) spectrum has been multiplied by 100.

Figure 7:
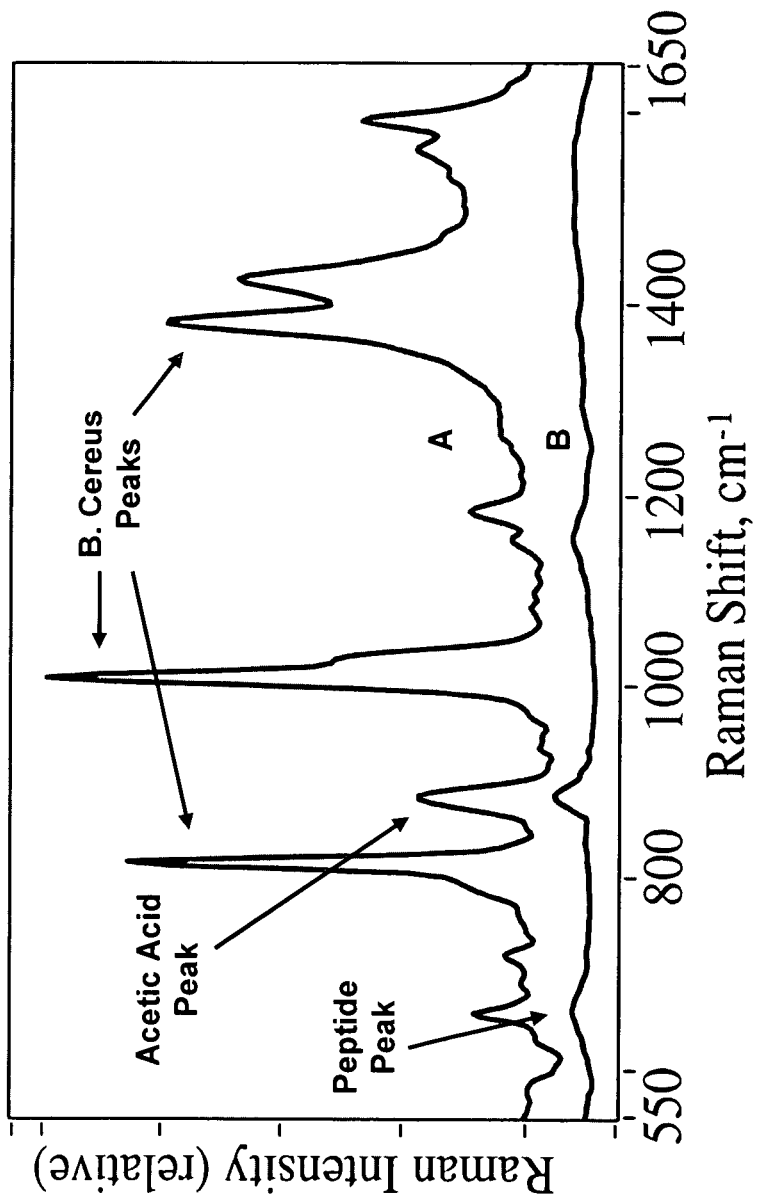

FIG. 7 comprises two SER spectra obtained for two different samples, A) containing 100 B. cereus and 10,000 B. subtilis spores in a 10 µL sample, and B) containing only 10,000 *B. subtilis* spores in a 10 μL sample, both introduced into identical 1 mm glass capillaries containing *B. cereus* specific peptides functionalized on silver in a sol-gel matrix. Both samples were allowed to bind for 5 minutes, washed with water, and further treated by addition of a silver colloid solution containing acetic acid to generate spectrum A and spectrum B, respectively.

FIG. 8 comprises two SER spectra obtained for 5000 *E. coli* O:157H:7 CFUs in a 50 μL sample added to two 1-inch glass disc coated with *E. coli* O:157H:7 specific antibodies functionalized on gold colloids. In both cases the samples were allowed to bind for 10 minutes, washed with water, air dried, and then, in the case of spectrum A but not in the case of spectrum B, further treated by the addition of a silver colloid solution.

FIG. 9 comprises two SER spectra of $10^7$ CFUs of A) *L. monocytogenes* and B) *L. innocua* on generalized *Listeria* antibody functionalized gold doped in a sol-gel matrix.

FIG. 10 is a plot of Principle Component Scores for 30 *Listeria* samples, consisting of 15 known *L. monocytogenes* (open circles) and 15 known *L. innocua* (open squares) and two correctly identified unknown samples (solid circle and solid square).

DETAILED DESCRIPTION OF THE PREFERRED AND ILLUSTRATED EMBODIMENTS

As indicated above, the present invention provides a novel method and apparatus to detect, identify, analyze, and quantify at least one target analyte, in a test sample that binds to target analyte-specific binding agent attached to a first SER-active material. A second SER-active material that binds to the binding agent is added, and the two SER-active materials act together, and in concert, to provide multiplicative signal enhancement for detection and analysis by SERS, affording substantial selectivity, sensitivity, and speed.

Turning now in detail to FIG. 1, therein illustrated, in each of the four depictions (A through D), is a substrate 1, such as may be made of metal, glass, paper, plastic or other suitable material, and may be a wall (i.e., an inside surface) of a vial, capillary or channel, or a plate or other structure described herein, coated with the first SER-active material 2 that is, in turn, functionalized with a binding agent 3. The binding agent 3 is attached to the SER-active material 2 by linking or spacing molecules 4. A blocking agent 5, attached to any unfunctionalized portion of the metal of the first SER-active material, is used to prevent any extraneous SER-active chemicals, biochemicals, or biologicals contained in the sample from interacting with the metal to produce an interfering SER spectrum.

In use, the analyte sample containing the target analyte 6, which may have been obtained by pretreatment of a test sample, is deposited on, or drawn across or through, the functionalized structure (1, 2, 3, 4, 5) by appropriate means, and allowed time to bind to the binding agent (shown as a second stage, in depiction B); preferably, the binding time is on the order of minutes. Any unbound or unwanted chemicals, biochemicals, or biologicals are then removed from the surface using a wash solution (not illustrated, but typically a component of the apparatus depicted in FIG. 2A), and a second SER-active material 7 is then introduced upon the surface (depiction C) so as to attach to the target analyte 6 (depiction D). The thus prepared and treated substrate is placed in an appropriate sample holder of a Raman spectrometer (not shown in this figure), by which the surface-enhanced Raman spectrum of the sample is recorded. Computer driven software then analyzes the spectrum to determine if the target analyte(s) are present and, if so, in what quantities.

FIG. 2A illustrates a kit that includes essential components of the apparatus of the present invention, contained in a case 9 of suitable construction. The contents of each kit will of course correspond to the application for which it is intended, but a main component is a SER-active sample device having an appropriate substrate coated with a functionalized gold- or silver-doped sol-gel, or other SER-active material, as described in the present specification. Such SER-active sample devices include internally coated or filled glass capillaries 10, a lab-on-a-chip device 12 having three internally coated or filled channels 14, a coated disc 16, or a coated multi-well plate 18.

As seen in FIG. 1 and FIG. 2.B, in all instances the SER-active device component includes a substrate 1, coated with a SER-active material 2, functionalized with a binding agent 3. It will be appreciated that the substrate 1 is generalized and will, as present in each of the several representative SER-active sample devices shown in FIG. 2A, have such curvature or other shape, and length, width, radial, etc. dimensions, as may be presented by the surface upon which the SER-active material and binding agent are to be attached.

In addition, the kit will contain the appropriate reagents contained in bottles or other containers, as necessary to carry out the method of the present method. However, a second primary component is a SER-active liquid reagent, such as a gold, silver, or other suitable metal colloid, as isolated spheres, clusters, aggregates, ring or tube structures, in container 20. Other reagents that may be necessary or desirable include water, in container 22, used in collecting samples and to wash away unbound chemicals in the substrates after the binding step; buffered solutions to collect nasal mucus or the like; digesting agents, such as NALC, to liquefy certain samples; and acetic acid, or the like, to degrade biologicals, as necessary. It will be appreciated that containers for the latter solutions, agents, and reagents are not illustrated, but will be of course be of suitable size and construction to best accommodate their contents. It will also be appreciated that the containers will advantageously have associated means for introducing their contents into the SER-active sample device included in the kit, such means being integral with the container (e.g., a normally closed spout), or separate therefrom but adapted for use therewith (e.g., syringe 23, a pipette 24, or the like).

A primary function of syringes 23, pipettes 24, and like components of course is to transfer liquids; they may for example be used to dispense water or other liquid onto a surface, to collect the possible pathogens present, or to introduce a sample into a SER-active sample device. Pipettes 24, syringes 23, and filter holders 32 included in the kit will desirably be constructed to connect to the corresponding included SER-active sample device. Connectors may however be included; for example, syringe ports may be provided for attachment to LOCs. Plunger-mounted swab 26 may be used to collect saliva or throat sputum, and its associated barrel 28 may be used to discharge the sample into a sample container, such as a vial 30. A filter holder 32, and replaceable filters 34, may be employed in either collecting or transferring a sample, as required, and additional vials will be supplied, as necessary, for sample collection, transfer, or mixing; even a blender (not shown) may be included in the kit for blending a sample, such as of food, with an extracting reagent, as may be necessary.

Figure 3:
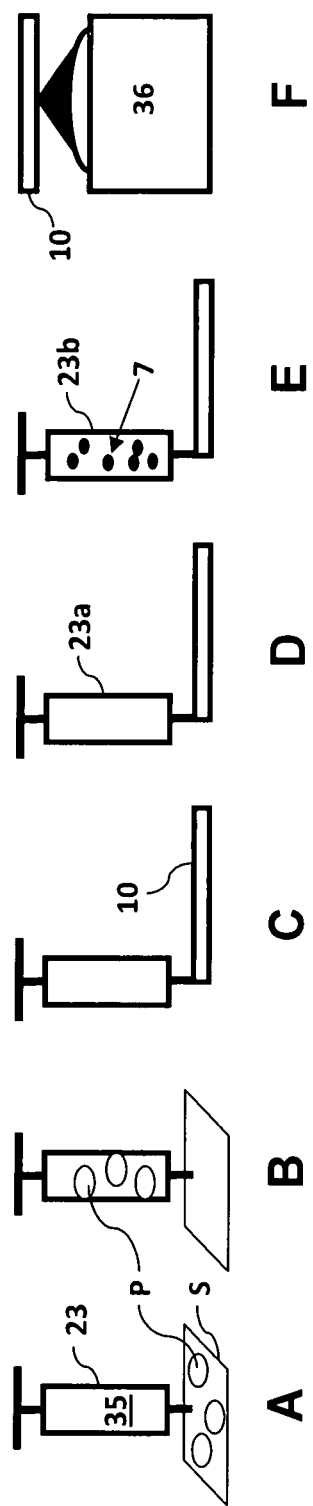

FIG. 3 shows the steps for measuring a pathogen sample on a surface by SERS, using a capillary that has been internally coated or filled with metal-doped sol-gel functionalized with an aptamer, antibody, peptide, protein, or the like. In accordance with step A, a reagent 35, such as water contained in a syringe 23, is squirted upon a surface S containing suspected pathogens P (i.e., the target analyte). In step B the reagent containing the target analyte (pathogens P), comprising the sample, is drawn back into the syringe. The sample is then injected, in Step C, into the capillary 10 containing the functionalized, metal-doped sol-gel, and allowed to bind for 5 minutes. A second syringe 23a is then used, in step D, to pass water through the capillary 10, thereby removing any unbound material. Then in step E a third syringe 23b is used to introduce metal colloids 7 into the capillary 10, in a volume sufficient to coat or fill the sol-gel portion. It is noted that it may be advantageous to add a reagent, such as acetic acid, to cause a marker chemical, such as dipicolinic acid, to be released before, with, or after the addition of the colloid 7. In step F the capillary 10 is mounted above the measurement point of a Raman spectrometer 36.

Figure 4:
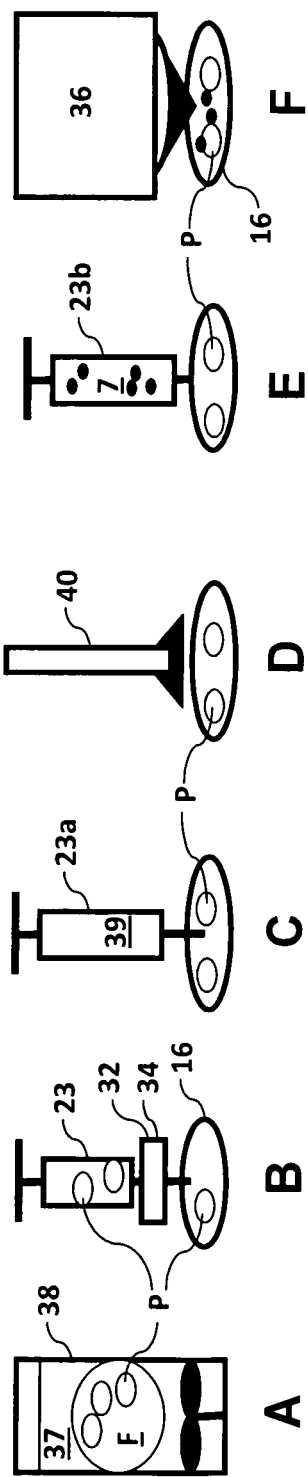

FIG. 4 shows the steps for measuring a food sample containing foodborne pathogens, by SERS, using a metal, glass, paper, plastic or other suitable material to form a planar substrate, such as the disc shown, coated with an antibody-functionalized SER-active material. In step A, a food sample F, potentially containing foodborne pathogens P as the target analyte, is placed in a blender 38 containing appropriate reagents 37. After blending, the sample is extracted into a syringe 23, in step B, and passed through a filter set 32, 34 to remove any undesirable chemicals and to deposit pathogens P onto a disc 16 coated with the functionalized SER-active material. In this case the sample is allowed to bind to the antibody for 20 minutes. A second syringe 23a, containing an appropriate reagent 39, is then used to gently wash the disc to remove any unbound material. Next the sample is dried, in step D, by blowing air onto it using an air hose 40. A third syringe 23b is then used, in step E, to introduce the second SER-active material 7, which could be silver colloid aggregates or ring structures, or gold-coated polystyrene or iron monospheres, onto the disc 16 in a volume sufficient to coat or fill the SER-active material deposit. Finally, in step F, the disc 16 is mounted below the measurement point of a Raman microscope system 36.

Figure 5:
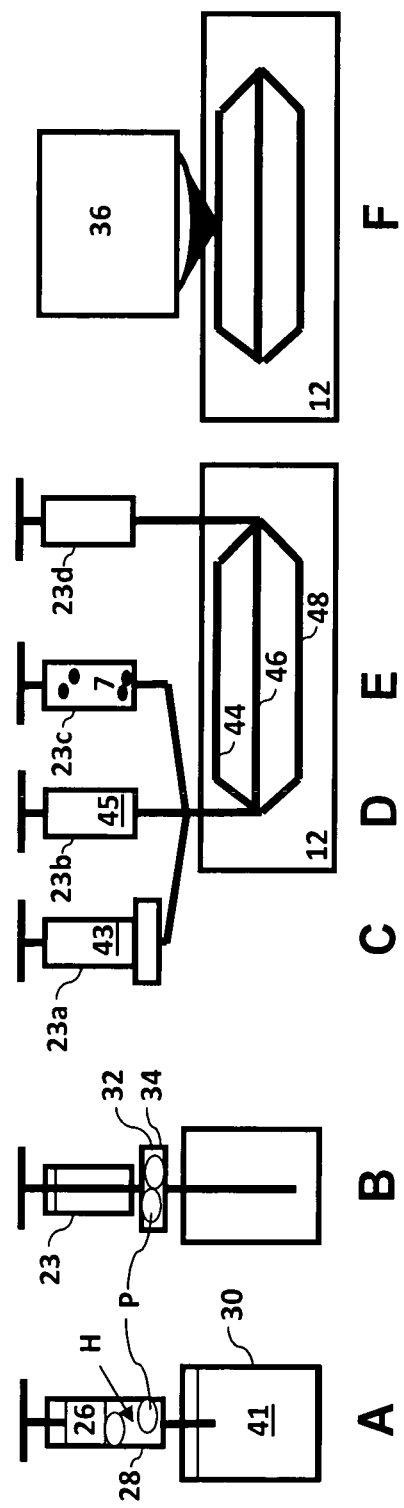
Figure 6:
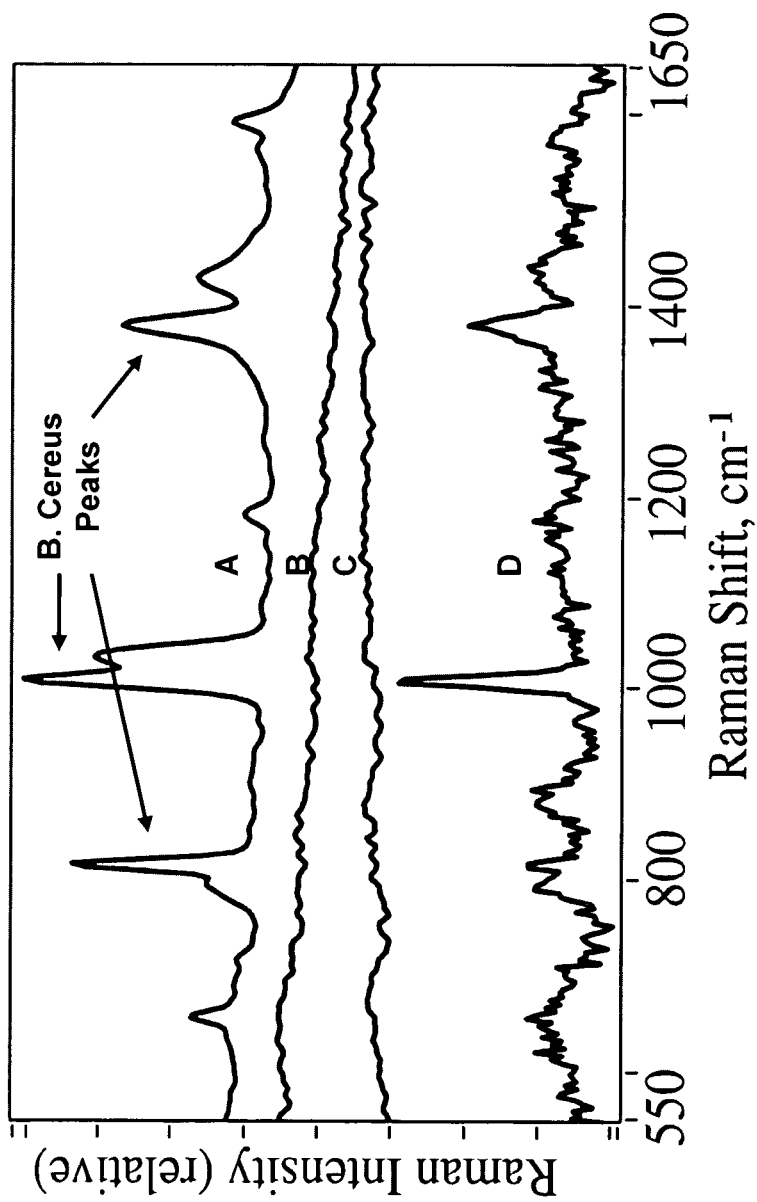

FIG. 5 shows the steps for measuring infectious disease pathogens by SERS using a lab-on-a-chip device having channels coated or filled with functionalized SER-active material, as described herein. As a first step A, a patient sample H, such as of saliva, nasal mucous, or throat sputum (containing suspected disease pathogens P), is collected using, for example, a swab 26, and is added, through a cooperating barrel 28, to vial 30 that contains a reagent 41 for liquefying the mucans of which such samples are comprised. After 2 minutes of mixing, the pathogen-containing reagent is drawn, in step B, by syringe 23 through a filter set 32, 34 through which the degraded mucans and undesirable chemicals are passed, but which captures the pathogens. In step C, a second syringe 23a, containing an appropriate reagent 43, is used to carry the captured pathogens into a lab-on-a-chip device 12. The LOC has three channels (in the illustrated embodiment), each functionalized with different antibodies or peptides designed to capture different pathogens; for example, channels 44, 46, 48 could be built to bind MRSA, TB, and NP, respectively. The channels may be arranged in parallel, as shown, or in series; i.e., comprised of a single channel with three different functionalized SER-active material segments. A third syringe 23b, containing an appropriate reagent 45, is then used in step D to wash the channels 44, 46, 48 so as to remove any unbound material; a fourth syringe 23c, is used in step E to introduce the second SER-active material, such as silver or gold colloids 7 in a volume sufficient to coat or fill the SER-active material containing portions of the channels; and a fifth syringe, 23d, may be used to control flow of the sample and reagents into the channels 44, 46, 48. Finally, in step F, the lab-on-a-chip device 12 is mounted below the measurement point of a Raman spectrometer 36 having the capability of scanning the three channels (or segments, as the case may be). It should be noted that the LOC employed herein can contain mixing chambers, controllable valves, and reagent wells, as described in U.S. Pat. No. 7,713,914, particularly noting FIG. 14 therein.

Exemplary of the efficacy of the present invention are the following specific examples:

Example One

*B. Cereus* Detected in a Peptide Functionalized Silver-Doped Sol-Gel Coated Capillary The silver-doped SER-active sol-gels employed in the filled glass capillaries utilized in this example were prepared in accordance with the method of Farquharson et al. (U.S. Pat. No. 6,623,977), which capillaries were filled with silver-doped sol-gels in accordance with the techniques described by Farquharson et al. ("Rapid dipicolinic acid extraction from *Bacillus* spores detected by surface-enhanced Raman spectroscopy" *Applied Spectroscopy,* 4, 351-354, 2004). In essence, a silver amine complex ($Ag(NH_3)_2^+OH^-$), consisting of a 5:1 v/v solution of 1 N $AgNO_3$ and $NH_4OH$ (28 wt % $NH_3$ in $H_2O$), was mixed with an alkoxide consisting of a 2:1 v/v solution of methanol and tetramethyl orthosilicate in a 1:8 v/v silver amine:alkoxide ratio. A 10 microL aliquot of the forgoing mixture was then drawn into a 1-mm diameter glass capillary to fill a 10-mm length. After sol-gel formation, the incorporated silver ions were reduced with dilute sodium borohydride, followed by a water wash to remove residual reducing agent.

Next, the silver particles contained in the sol-gel were functionalized with a peptide binding agent designed to specifically bind *B. cereus*. Functionalization was accomplished by attaching a cysteine residue to the C-terminus of the peptide and adding it to the silver-doped sol-gel. Cysteine serves as a link, as it forms a covalent bond to the silver between its thiol group and silver. It also serves as a spacer, in that the peptide is displaced from the silver surface by about 2-10 angstroms, providing space therebetween within which the spores can effectively bind. The functionalized sol-gel was then washed with a solvent to remove any unbound peptide.

A first set of experiments, designated Part 6A through Part 6D, was performed to illustrate the concerted, multiplicative effect of using two SER-active materials in accordance with the present invention; the data obtained are graphically presented as Spectra A through D in FIG. 6:

Part 6A

A 10 microL sample containing 1000 *B. cereus* spores was injected into a capillary, as described above, using a syringe. The volume of the sample matched the volume defined by the diameter of the capillary and the length coated with peptide-functionalized silver-doped sol-gel. A period of 5 minutes was allowed for the sample to bind (it is noted that in some instances it is advantageous to draw more of the sample through the capillary, to introduce more spores to the binding sites, but at a slow rate to allow binding). A 20 microL wash solution was drawn through the capillary to remove any unbound or unwanted chemicals, biochemicals, or biologicals. Then a solution containing silver colloids, prepared in accordance with Lee and Meisel ("Adsorption and Surface-Enhanced Raman of Dyes on Silver and Gold Sols", *J. Phys Chem.*, 86, 3391-3395, 1982), was injected by syringe into the capillary, again matching the volume defined by the capillary diameter and SER-active coating length. The capillary was placed in a capillary holder of an FT-Raman spectrometer, and the SER spectrum of the sample was recorded in 1 minute using 75 mW of 785 nm laser power. The entire measurement, from sample introduction to spectral analysis, took less than 10 minutes. The resultant spectrum, designated A, in FIG. 6, shows the unique spectrum of dipicolinic acid with major peaks at 815, 1008, 1382 and 1428 $cm^{-1}$, which identify the presence of the *B. cereus* spores. It is worth noting that the signal-to-noise ratio (S/N) for the 1008 $cm^{-1}$ peak is ca. 600, suggesting a detection limit based on a S/N of 3 equivalent to 5 *B. cereus* spores.

Part 6B

Another 10 microL sample containing 1000 *B. cereus* spores was injected, by syringe, into the capillary of a second, identical silver-doped SER-active sol-gel filled glass capillary, prepared identically to the one described in Part 6A above. The same procedure was used, but no colloids were added to the capillary after the sample wash. The resultant SER spectrum, designated B in FIG. 6, shows no indication that the spores are present, and hence the use of a first SER-active material functionalized to bind *B. cereus* alone was insufficient to produce a SER signal.

Part 6C

In a third part of this experiment an identically prepared capillary was again used, but with the silver amine complex being omitted. The sol-gel did not therefore contain any silver particles, nor could it be functionalized with the peptide. Nevertheless, a sample and silver colloids were added at the same concentrations as in the Part 6A measurement, but with the wash step being omitted to avoid removal of the spores and colloids. The resultant SER spectrum, designated C in FIG. 6, shows no indication that the spores are present, which demonstrates that the addition of a second SER-active material, here silver colloids, was insufficient to produce a SER signal.

Part 6D

To establish that the colloids and spores were in fact present in the sample of Part C, the same experiment was repeated once again, but with acetic acid added to the analyte sample. The resultant spectrum, designated D in FIG. 6, contains the characteristic DPA peaks, confirming the presence of the spores and colloids, but at an intensity about 100 times less than that which was produced in the initial measurement, spectrum 6A.

Part 7A

A second set of experiments was performed to illustrate the selectivity of the peptide binding agent; the data obtained are graphically presented as Spectra A and B in FIG. 7:

A 10 microL sample containing 100 *B. cereus* and 10,000 of *B. subtilis* spores was injected into a capillary, again prepared as described previously in this example; the volume of the sample matched the volume defined by the diameter of the capillary and the length coated with peptide-functionalized silver-doped sol-gel. A period of 5 minutes was allowed for the sample to bind, following which a 20 microL wash solution was drawn through the capillary to remove any unbound or unwanted chemicals, biochemicals, or biologicals; in this case, the *B. subtilis* spores are unwanted biologicals. Then a solution containing silver colloids was injected by syringe into the capillary, once again matching the volume defined by the capillary diameter and SER-active coating length, but in this case the silver colloid solution also contained acetic acid to promote the rapid release of dipicolinic acid, as discussed above and disclosed in U.S. Pat. No. 7,713,914. The capillary was then placed in a capillary holder of an FT-Raman spectrometer, and the SER spectrum of the sample was again recorded in 1 minute using 75 mW of 785 nm laser power. The resultant spectrum, designated A in FIG. 7, shows the unique spectrum of dipicolinic acid which, assuming the binding was specific, identifies the presence of the *B. cereus* spores, as is verified by the next part of this experiment.

Part 7B

A second 10 microL sample containing only the 10,000 *B. subtilis* spores was measured using a procedure identical to Part 7A. The resultant spectrum, designated B in FIG. 7, is seen to contain only a weak acetic acid peak at 880 $cm^{-1}$ and two weak peptide peaks at 660 and 1180 $cm^{-1}$, with dipicolinic acid peaks no longer being present. This, and the measurement of the previous part, demonstrates that the peptide does not bind *B. subtilis* but selectivity binds *B. cereus.*

Based on the relative concentrations for the 100-spore and 1000-spore *B. cereus* samples measured using the two SER-active materials acting in concert, versus use of the colloids alone, and the corresponding intensities of the DPA peak at 1008 $cm^{-1}$ shown in spectrum A of FIG. 7 and spectrum D of FIG. 6 (the FIG. 7A 1008 $cm^{-1}$ spectral peak intensity equals 100 times the 6D spectral peak), the additional signal enhancement achieved by the method and apparatus of the present invention is about 1000 times. It will be appreciated that this result is completely unexpected, based upon the knowledge of those of ordinary skill in the art and upon previously published measurements described in the literature.

As will also be appreciated, in the case of an unknown sample, the number of *B. cereus* spores can be quantified by comparing the intensity of any of the primary peaks, such as the ring breathing mode at 1008 $cm^{-1}$ to the intensity of the Cys-Ag stretching peptide mode at 660 $cm^{-1}$, so long as a relationship between the peak intensity ratios to spore count has been established. The acetic acid solvent peak, at 880 $cm^{-1}$, can be used to the same purpose of quantifying the number of spores present.

It should of course be realized that the invention, as illustrated by the present example, would be of particular benefit to homeland and military security activities when used to selectively detect *B. anthracis*, such as by the detection of spores in ambient air, in mail, on surfaces, or even in nasal mucus, throat sputum, or saliva. Furthermore, it will be appreciated that the method and apparatus of the invention could be expanded to include all bioagents, provided that an appropriate binding agent, such as a peptide, an aptamer, or an antibody, was employed.

Example Two

Measurement of *E. coli Detected on an Antibody Functionalized Gold Colloid Coated Glass Slide*

Part 8A

A gold colloid solution was prepared according to Pal et al. ("Photochemically prepared gold nanoparticles: A substrate for surface enhanced Raman scattering," *Current Sci.,* 84, 1342-1346, 2003). One-inch diameter glass discs were spin-coated at 2500 rpm by adding 1 mL of the gold colloid solution drop-wise to form a monolayer. Once the coating dried, a layer of multifunctional polyethylene glycol ligands—a linker, containing two thiol groups for anchoring onto the gold and a terminal N-hydroxysuccinimide ester group for coupling to antibodies, was added to the surface. After 4 hours the discs were washed with water to remove any unbound PEG from the gold surface. The *E. coli* selective antibody was then added to the surface and allowed to functionalize over a period of 2 hours, and another buffer wash was thereafter used to remove any unfunctionalized antibody. Then a solution of polylysine was added to the disc to block any of the gold surface not functionalized with the antibody, and the resulting structure was also washed with a buffer to remove any polylysine that might attach to the antibody. Previous measurements of adenine, with and without the blocking agent, produced a SER spectrum of adenine only when the blocking agent was not used, thus verifying the effectiveness of the blocking agent.

Part 8B

Figure 8:
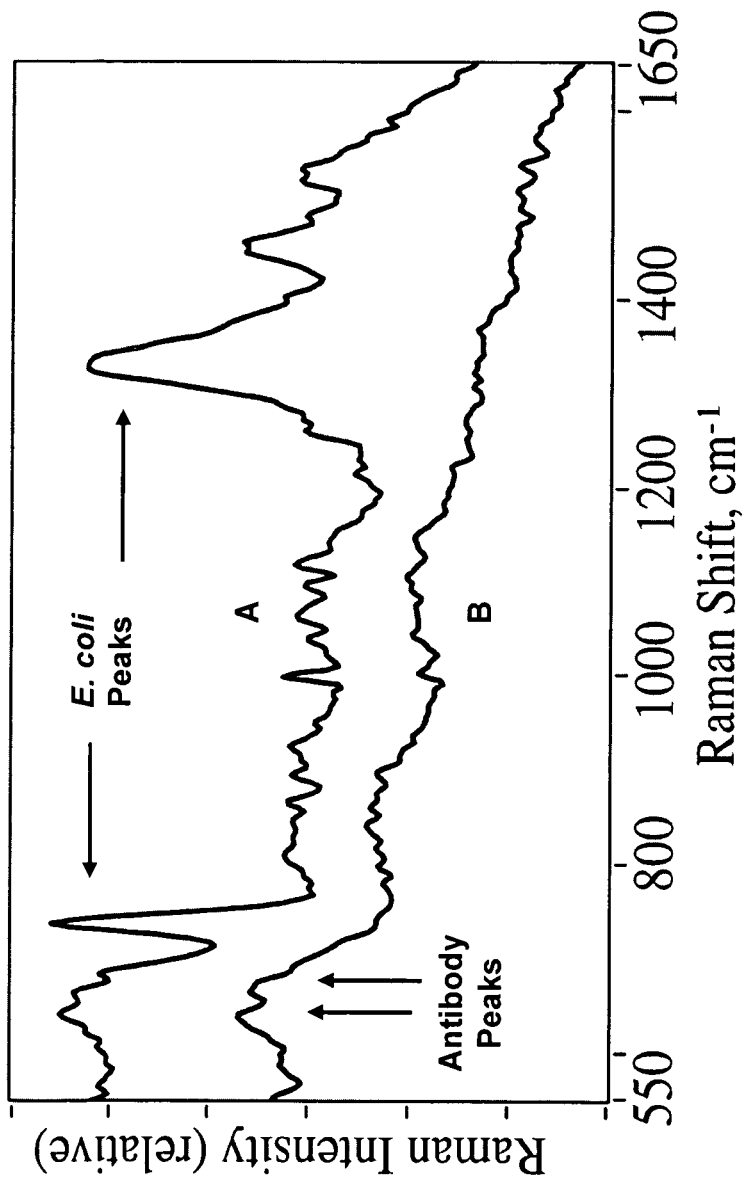

A sample of lettuce was inoculated with 1,000,000 *E. coli* colony-forming units. The test sample was blended in water to produce an approximately 100,000 *E. coli* CFU per 1 mL lettuce-water solution. A 1 mL sample was pushed through a filter to remove the degraded lettuce while passing the CFUs, to produce an analyte sample, 50 microL of which was deposited onto the antibody-functionalized gold colloid-coated glass slide. After allowing a 20-minute binding period, the surface was gently washed with a reagent to remove any undesired or unwanted chemicals, biochemicals, or biologicals. The sample was then force dried with blowing air, followed by the addition of 50 microL of a silver colloid solution, during a period of about 3 minutes. The glass slide was placed at the focal point of a Raman microscope and recorded in 1 minute using 75 mw of 785 nm laser excitation. The resultant spectrum, designated A in FIG. 8, shows two peaks at 740 or 1340 $cm^{-1}$ indicative of *E. coli*. Once again, the same sample was measured identically, but without the addition of colloid. The resultant spectrum, designated B in FIG. 8, only shows the SERS of the antibody, a doublet at 640 and 665 $cm^{-1}$, again demonstrating the importance of the second SER-active material acting in concert with the first. Furthermore, the intensity ratios of the *E. coli* peaks in spectrum A to the antibody peaks in spectrum B, can be used to determine that the 50 microL sample contained ca. 5000 *E. coli* CFU, provided that a correspondence between the ratio of known concentrations has been established.

It should be noted that in some cases it is important to differentiate pathogen species, subspecies, strain or serotype, but unique peptides or antibodies for each species, subspecies, strain or serotype are not always known, only generic binding agents are known. It may still be possible however to identify the species, subspecies, strain or serotype if the Raman spectra are different, but the differences in the spectra may be subtle, requiring the use of chemometrics, statistics applied to chemistry.

Figure 9:
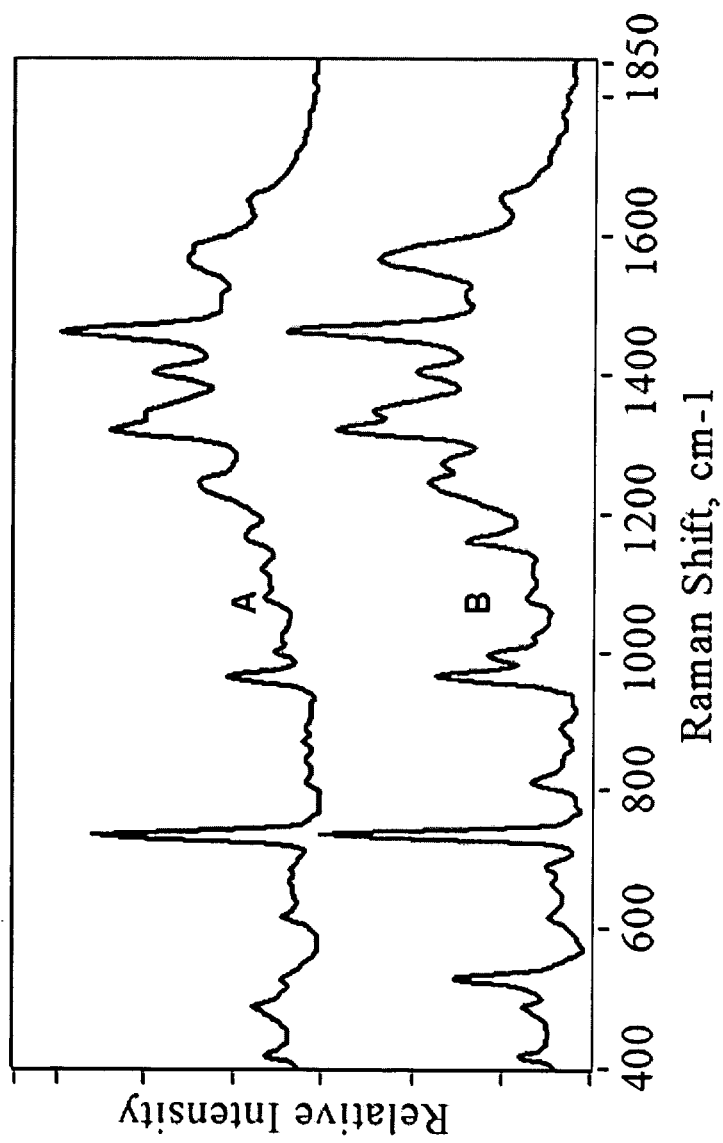

As an example, fifteen 5000 CFUs per 50 microL samples each of *Listeria monocytogenes* and *Listeria innocua* were prepared and measured on fifteen separate SER-active sample devices as described for *E. coli*, but functionalized with a generic *Listeria* antibody as the binding agent. FIG. 9 shows the SERS of the averaged spectra for the two species within the *Listeria* genus; modest spectral differences are apparent. Software was used to develop a simple discriminate linear regression model using principal component analysis that employed a series of weighted spectral regions that correlate to the two different *Listeria* species, as shown in FIG. 10.

Figure 10:
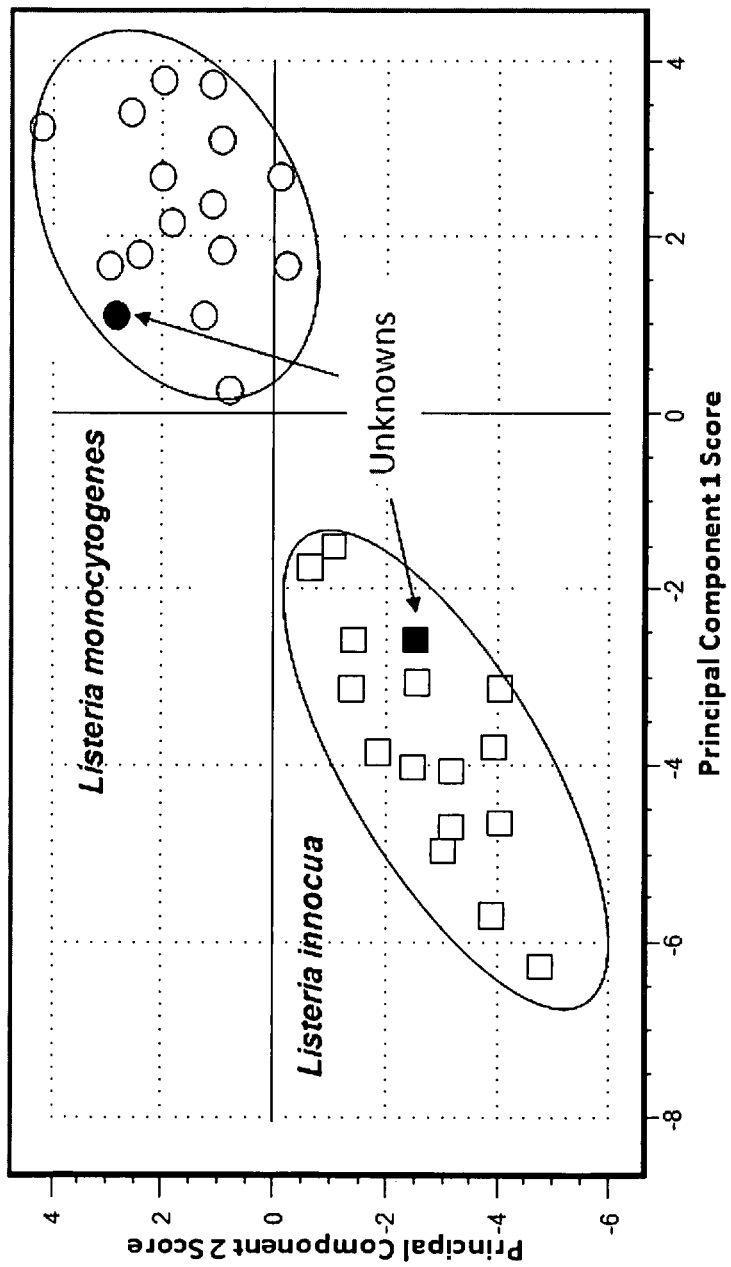

Then two additional discs were prepared as above, functionalized with the generic *Listeria* antibody, and used to measure two samples designated unknowns in FIG. 10, one containing *L. monocytogenes* and one containing *L. innocua*. The spectra were then analyzed in terms of the Principal Component Scores, which placed them within the species regions allowing the identification of the *Listeria* species contained in each sample.

It should be realized that such chemometric-based relationships can be developed for a number of target analyte properties as part of the analysis of the present invention, such as pathogenicity, potency, toxicity, and viability. Other linear regression models, such as principal component regression analysis, partial least squares, classical least squares, inverse least squares, or even higher-order models might of course also be used to develop such a relationship.

Example Three

Measurement of Hospital Pathogens: Methicillin Resistant *Staphylococcus aureas* (MRSA), *Tubercles bacillus* (TB), and *Nosocomial pneumonia* (NP)

As described hereinabove in connection with FIG. 5, a lab-on-a-chip device is designed with three channels, each containing a SER-active metal functionalized with a different binding agent (peptide, aptamer, antibody, etc.) for selectively binding MRSA, TB or NP. In some instances the SER-active metal is chemically attached to the walls of the channels; in other cases it is contained in the channel, preferably incorporated in a sol-gel. A throat sputum sample, collected from a hospital patient, is treated with reagents, such as N-acetyl-L-cysteine and sodium hydroxide, to liquefy the mucans that potentially contain the target hospital pathogens, as described in U.S. Pat. No. 7,713,914. The sample is filtered to trap the pathogens, while passing the mucans and other potentially interfering biochemicals, after which the pathogens are collected and added to a solvent. The resultant pathogen sample is then injected or drawn into the LOC, by syringe or other means, in such manner that it is equally divided among the three channels and so that, if present, the pathogens bind to their respective binding agents. A wash solution is injected or drawn through the three channels of the LOC to remove any unbound pathogens or potentially interfering chemicals or biochemicals, following which a solution containing silver colloids is injected or drawn through the channels so as to optimize, acting in concert with the resident SER-active metal within the channels, the SER signal ultimately generated, in accordance with the present invention. Thus, the LOC is placed on a sample stage constructed so as to be capable of aligning each channel with the Raman excitation laser, and the SER spectra are recorded. Software is used to analyze the spectra and determine if any of the three pathogens are present and, if so, in what quantity.

It will be readily apparent to those skilled in the art that the method and apparatus described herein can be utilized to detect and quantify other pathogens contained in body fluids, such as cholera, hepatitis, human immunodeficiency virus, influenza, malaria, and strep throat, as well as alternatives to the numerous other target analytes specifically mentioned herein. For example, the method and apparatus can be used to identify biomarkers in body fluids, indicative of a disease or deleterious health state, such as for the detection of antigen 3 in urine, indicative of prostate cancer, or cholesterol in blood, indicative of hardening of the arteries.

As noted previously, the three channels of the LOC described could be replaced with a single channel containing each of the binding agents, functionalized on metal particles, spaced in sequence; or the binding agents could all be in a single sol-gel mixture. In the former case, but not the latter, a positioning stage would still be required; in the latter case, however, spectral analysis could be used to deconvolute the contributions from each bound pathogen, so long as the spectrum for each pathogen is unique. Needless to say, an LOC employed herein can have any suitable number of channels, and/or sequential deposits, and/or binding agent species, as dictated by the objectives of the analysis and practical considerations. In certain embodiments, moreover, an LOC can contain liquefying reagents, filters, and SER-active colloids in reservoirs, as indicated, for example, in FIG. 14 of U.S. Pat. No. 7,713,914.

Example Four

Measurement of Usher Syndrome (Blindness and Deafness) Gene in Parental DNA

Prior to having children, many parents, especially those with a family history of health problems, have DNA testing performed to determine the risks of passing on a disease. The present example addresses that concern.

A monolayer of polystyrene latex spheres of uniform 40 nm diameter size are spin coated onto a glass disc, dried, and overcoated with a thin layer of silver using a thermal evaporation chamber, as described by Vo Dinh, et al. (Surface-enhanced Raman spectrometry for trace organic analysis", *Anal. Chem.*, 56, 1667, 1984). The silver is then functionalized with oligonucleotide #1 via an aliphatic thiol that serves to both link the oligonucleotide to the metal and as a 2-10 angstrom spacer to provide sufficient room above the metal surface so binding can occur unhindered. The oligonucleotide can consist of any number of nucleotides bound together, but preferably they are relatively short, containing 10 to 20 units; such nucleotides are often referred to as DNA or RNA aptamers. A solution of bovine serum albumin is added to the functionalized silver substrate, which binds to any exposed silver, blocking the surface from extraneous SER-active chemicals, biochemicals, or biologicals contained in the analyte sample that might interact with the metal and produce an interfering SER spectra.

SER-active gold colloids that are also magnetic are prepared according to the procedure of Mosier-Boss ("Surface-enhanced Raman spectroscopy substrate composed of chemically modified gold colloid particles immobilized on magnetic microparticles", *Anal. Chem.*, 77, 1031, 2005). In essence, gold colloids are bound to amine-terminated iron oxide microparticles and, after several hours of mixing, a magnet is used to separate the gold colloid-coated iron oxide microparticles. Oligonucleotide #2 is attached to those particles via an aliphatic thiol that, as above, serves to both link the oligonucleotide to the metal and provide unhindered binding room.

Both aptamers are compliments to two different DNA targets contained within the MY07A gene, which is associated with Usher Syndrome. A purified DNA sample, obtained from prospective parents, that has been fragmented using restrictive enzymes or other techniques known to those skilled in the art, is added to the aptamer-functionalized silver substrate (as a SER-active sample device), and the MY07A gene fragments, if present, are allowed to bind i.e. hybridize, for 15 minutes at 37° C. The silver substrate is washed to remove any unbound sample. The functionalized gold microparticles are then added to the functionalized substrate. A magnet, placed below the silver substrate, is used to speed the interaction between the oligonucleotide #2 and its complement on the MY07A gene fragments bound to the substrate via oligonucleotide #1, if present. The magnet is removed, and the substrate is washed to remove any unbound gold particles. The SER-active sample device is placed in the sample compartment of a Raman spectrometer, and the spectrum is measured and analyzed.

If the MY07A gene is not present, then either a relatively weak spectrum of oligonucleotide #1 is obtained, or if a complement to oligonucleotide #1 is present, but not due to the MY07A gene, then a weak spectrum of the complimentary, hybridized sequence is obtained. If however the MY07A gene is present, then an intense spectrum of both complimented oligonucleotide #1 and #2 is obtained. The dramatic increases in sensitivity, attributable to the use of a second SER-active particle in accordance with the present invention, and in selectivity due to the two sequences, allows performing this measurement in as brief a period as 20 minutes, substantially faster than the current 2 to 6 hours' time required by PCR.

Again, the present invention could be applied to the detection of all genetic diseases for which the genetic sequences are known or become known. Furthermore, as described above, an LOC could be designed to detect any of numerous genetic diseases.

Example Five

Drug Discovery Using a Multi-Well Microplate

Drug discovery involves methods that screen the activity of numerous potential drugs by examining their interaction with a disease or health target which, in accordance with the present invention, would be the binding agent. In such cases the binding agent could be a simple nucleotide or a protein which represents the binding site for potential drugs designed to cure a disease. For example, the binding agent could be an enzyme involved in cancer growth which, if inhibited by the drug, would arrest the cancer.

In accordance with this Example, each well of a 384-well microplate is bottom-coated with a first SER-active material by introducing thereinto, and drying, a 10 microL gold colloid solution. A solution containing a binding agent then is added to each well. A linking species, such as a sulfur containing chemical or biochemical, may be added to the binding agent so that it forms a covalent bond with the gold surface. One of as many as 384 potential drugs, in a solvent such as water, is added to each well, followed by flushing, using 10 microL solvent, to remove any unbound drugs. Then a 10 microL silver colloid solution is added to each well. The microplate, as the SER-active sample device, is thereafter placed on a sample stage that is capable of aligning each well with a Raman excitation laser, and the SER spectra are recorded. If no drug is present only a weak binding agent SER signal will be observed. If, however, a drug binds to a protein binding site, then an intense SER signal of the potential drug or it's metabolites will be produced even at exceptionally low concentrations, such as 1 ng/mL.

Here again it will be appreciated by those skilled in the art that the method and apparatus described in this Example could be used to discover, in addition to drugs, many important chemicals, biochemicals or biologicals. For example, a microplate filled with a particular pathogen as the binding agent could be used to examine a series of peptides or antibodies so as to identify a peptide or antibody that binds to the pathogen.

Example Six

Identification of Effective Antibiotic and Antiviral Drugs for Pathogens

The approach described in Example Five is readily adapted for the identification of effective antibiotic and antiviral drugs for pathogens. To do so, for example, each well of a 96-well SER-active microplate is functionalized with a binding agent designed to capture a target pathogen (e.g. methicillin resistant *Staphylococcus aureus*, H1N1 virus, *Plasmodium falciparum*, etc.). To each such functionalized well, 10 microL of a pathogen suspension is added and allowed to attach to the well surface for 15 minutes, after which the wells are flushed with a buffer solution to remove any unbound pathogen. Then 10 microL aliquots, of as many as 96 potential drugs in their respective solvents, are added, one each to a well, and the drug solutions are allowed to bind to the target pathogen for 30 minutes, for example. The wells are then washed with a solvent to remove any unbound drug molecules, following which a 10 microL silver colloid solution is added to each well. The microplate is placed on a sample stage and, as previously described, SER spectra are recorded, but with each well being measured for 5 seconds, in sequence, thus requiring a total of only 8 minutes' time to measure the 96 wells. This procedure is repeated through a period of 2 hours, for example, thereby providing 15 time-dependent spectra for each well so as to efficiently monitor the effectiveness of each drug.

For drugs that are effective against the target pathogen, not only will they produce intense SER spectra of the drugs or their metabolites, indicating binding, but changes in the pathogen spectral fingerprints are observed over time. If the drug molecules are not effective, the pathogen spectral features would not change over time.

Thus, it can be seen that the present invention provides a novel method and apparatus for detecting, identifying, analyzing, and quantifying, in a test sample, target analyte(s) that bind to target analyte-specific binding agents. More specifically, it provides such a method and apparatus wherein analyses are effected by surface-enhanced Raman spectroscopy, with substantial selectivity, sensitivity, and speed, through multiplicative signal enhancement.

Having thus described the invention, what is claimed is:

1. A method for the detection, identification, analysis and quantitation, by surface-enhanced Raman spectroscopy, of at least one designated target analyte, comprising the steps:
   providing a support structure comprised of a first, SER-active metal-containing SER-active material;
   providing a liquid reagent comprised of a second, SER-active metal-containing SER-active material;
   functionalizing the SER-active metal of at least one of said first and second SER-active materials with at least one binding agent that has a specific capability for binding thereto at least one designated target analyte, to provide at least one functionalized SER-active material, said at least one binding agent being a chemical, biochemical, or biological substance and being attached to said SER-active metal of said at least one functionalized SER-active material by means of covalent, ionic, or hydrogen bonding, or by van der Waals interactions between charged, polar, hydrophobic, or hydrophilic chemical groups on a surface of said at least one binding agent, or by a combination of at least one of said means of bonding and at least one of said interactions;
   obtaining an analyte sample suspected of containing said at least one designated target analyte, said at least one designated target analyte being a chemical, biochemical, or biological substance;
   adding said analyte sample to one of said at least one functionalized SER-active materials;
   establishing or maintaining conditions sufficient to effect attachment of said at least one designated target analyte to said at least one binding agent of said one functionalized SER-active material by said means of bonding, said interactions, or said combination of at least one of said means of bonding and at least one of said interactions;
   effecting the removal of any unbound chemical, biochemical, or biological substances from said one functionalized SER-active material to which said at least one target analyte is attached;
   adding said liquid reagent to said support structure;
   establishing or maintaining conditions effective to cause the other of said first and second SER-active materials to attach to said at least one target analyte already attached to said at least one binding agent of said one functionalized SER-active material by means of covalent, ionic, or hydrogen bonding, or by van der Waals interactions between charged, polar, hydrophobic, or hydrophilic chemical groups on the surface of said at least one binding agent, or by a combination of at least one of said means of bonding and at least one of said interactions;
   irradiating said first and said second SER-active materials attached to said at least one target analyte so as to cause said SER-active metals of said SER-active materials to cooperatively generate a SER spectrum;
   detecting said cooperatively generated SER spectrum; and
   analyzing said detected SER spectrum to determine the presence and quantity of said at least one designated target analyte.

2. The method of claim 1 wherein said first SER-active material is comprised of at least one chemically synthesized porous material.

3. The method of claim 2 wherein said at least one binding agent, said liquid reagent comprised of said second SER-active material, said at least one designated target analyte, and any signature chemical that may be present, can readily pass through said at least one chemically synthesized porous material.

4. The method of claim 3 wherein said chemically synthesized porous material is effective to separate said at least one designated target analyte from other components of said analyte sample.

5. The method of claim 1 wherein the effects of said SER-active metals attached to said at least one target analyte, in cooperatively generating said SER spectrum, are synergistic.

6. The method of claim 1 wherein said support structure comprises a substrate supporting said first SER-active material.

7. The method of claim 6 where said substrate is fabricated from metal, glass, paper, or plastic, and is in the form of a substantially planar sheet, plate, or membrane.

8. The method of claim 7 wherein said substrate has a multiplicity of wells formed thereinto for receiving said analyte sample.

9. The method of claim 6 wherein said substrate is fabricated from glass or plastic and is in the form of a wall of a vial, capillary, or channel.

10. The method of claim 1 wherein a linker chemical or biochemical substance is interposed for attaching said at least one binding agent to said SER-active metal of said at least one functionalized SER-active material.

11. The method of claim 10 wherein the molecule of said linker chemical or biochemical substance contains sulfur.

12. The method of claim 1 wherein a spacer chemical or biochemical substance is interposed effectively between said at least one binding agent and said SER-active metal of said at least one functionalized SER-active material to provide sufficient space for the at least one target analyte to attach to said at least one binding agent.

13. The method of claim 1 wherein a blocking chemical or biochemical substance is added to said at least one functionalized SER-active material to prevent extraneous SER-active chemical, biochemical, or biological substances contained in the analyte sample from interacting with said SER-active metal of said at least one functionalized SER-active material so as to thereby minimize the production of SER spectra that would interfere substantially with a spectrum of said at least one designated target analyte.

14. The method of claim 1 wherein said SER-active metal of each of said first and second SER-active materials is selected from the group consisting of copper, gold, silver, nickel, platinum, rhodium, iron, ruthenium, cobalt, nickel, palladium, and alloys and mixtures thereof.

15. The method of claim 14 wherein said SER-active metals of said first and second SER-active materials are different from one another.

16. The method of claim 1 wherein said SER-active metal of said first SER-active material is of particulate form or in the form of a surface having a morphology that is functionally equivalent to metal particles for generating a plasmon field when irradiated, and wherein said SER-active metal of said second SER-active material is of particulate form.

17. The method of claim 1 wherein said at least one binding agent and said at least one designated target analyte are paired with one another for effective interbonding, such pairs being selected from the group consisting of (a) antibodies and antigens, (b) peptides and biologicals, (c) drug receptors and drugs, (d) enzymes and their specific biochemical substrates, (e) carbohydrates and lectins, and (f) nucleic acid sequences and their complements.

18. The method of claim 1 wherein said at least one target analyte sample comprises a biological agent.

19. The method of claim 18 wherein said biological agent is selected from the group consisting of *Bacillus anthraces, Clostridium botulinum* A, Dengue fever, Ebola virus, *Francisella tularensis, Leishmania* genus, Marburg virus, *Mycobacterium leprae, Plasmodium* genus, Puumala hantavirus, Ricin toxin, Variola virus, and *Yersinia pestis.*

20. The method of claim 1 wherein said at least one target analyte sample comprises a foodborne or waterborne pathogen.

21. The method of claim 20 wherein said foodborne or waterborne pathogen is selected from the group consisting of *Aeromonas hydrophilia, Bacillus cereus, Campylobacter jejuni, Clostridium botulinum* B and C, *Clostridium difficile* and *perfringens, Cryptosporidium parvum, Escherichia coli, Giardia lamblia,* Hepatitis A, *Listeria monocytogenes* and subspecies thereof, *Salmonella enterica, typhimurium* and subspecies thereof, *Shigella, Yersinia enterocolitica.*

22. The method of claim 1 wherein said at least one target analyte is a disease-causing pathogen.

23. The method of claim 22 wherein said disease-causing pathogen is selected from the group consisting of *Burkholderia mallei,* coronaviruses, *Corynebacterium diphtheriae,* Enteric viruses, *Enterobacter aerogenes, Equine encephalitis,* hemorrhagic fevers, Hepatitis A through E, herpes simplex viruses 1 and 2, human immunodeficiency virus, *Legionella,* Lyme *borreliosis,* measles, meningitis, mumps, MRSA, *Mycobacterium tuberculosis, Mycoplasma pneumonia, Neisseria gonorrhoeae,* Norwalk virus, members of the Orthomyxoviridae family, rabies virus, rhinoviruses, Rubella virus, saxitoxin, sepsis, *Shigella* subspecies, and *dysenteriae,* Staphylococcal, *Streptococcus pneumonia,* Swine disease, *Treponema pallidum, Vibrio cholerae, Varicella zoster* virus, West Nile virus, and Yellow fever.

24. The method of claim 1 including the further step of adding to said analyte sample at least one reactive reagent that is effective to react, under the conditions existing or established, with a constituent of said analyte sample for releasing a signature chemical substance, a signature biochemical substance, or a signature biological substance, said signature chemical, biochemical, or biological substance constituting said at least one designated target analyte.

25. The method of claim 24 wherein said at least one target analyte is a released signature biochemical substance selected from the group consisting of amino and nucleic acids, nucleotides, nucleosides, peptides, proteins, lipids, polysaccharides, haptans, antibodies, antigens, biomarkers, enzymes, steroids, hormones, lectins, aptamers, and fragments and polymers thereof.

26. The method of claim 24 wherein said at least one target analyte is a released signature chemical substance selected from the group consisting of calcium dipicolinate, dipicolinic acid, mono-protonated dipicolinic acid, deprotonated dipicolinic acid, diaminopimelic acid, n-acetyl-muramic acid, ribonucleic acid, phosphoglyceric acid, and sulfoacetic acid.

27. The method of claim 1 wherein said support structure is constructed to effectively enable irradiation of said at least one designated target analyte and said first and second SER-active materials, and detection of said cooperatively generated SER spectrum.

28. The method of claim 1 wherein a chemometric technique is applied to augment at least one of detection, identification, analysis, and quantitation of the at least one target analyte.

29. The method of claim 28 wherein said chemometric technique applied augments analysis for the determination of pathogenicity, potency, toxicity or viability.

* * * * *